United States Patent
Hou et al.

(10) Patent No.: US 12,257,365 B2
(45) Date of Patent: Mar. 25, 2025

(54) INCISED DESCEMET'S MEMBRANE AND METHODS OF MAKING AND USING

(71) Applicant: Regents of the University of Minnesota, Minneapolis, MN (US)

(72) Inventors: Joshua Honghan Hou, Minneapolis, MN (US); Peter Bedard, St. Paul, MN (US); Jeffrey Joseph Justin, St. Paul, MN (US); Mark Spencer Hansen, Long Lake, MN (US); Martin de la Presa, Roseville, MN (US); David Ronald Hardten, Excelsior, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 727 days.

(21) Appl. No.: 16/858,299

(22) Filed: Apr. 24, 2020

(65) Prior Publication Data
US 2020/0338235 A1    Oct. 29, 2020

Related U.S. Application Data

(60) Provisional application No. 62/838,986, filed on Apr. 26, 2019.

(51) Int. Cl.
*A61L 27/38*    (2006.01)
*A61F 2/14*    (2006.01)
*A61L 27/36*    (2006.01)

(52) U.S. Cl.
CPC .......... *A61L 27/3839* (2013.01); *A61F 2/142* (2013.01); *A61L 27/3691* (2013.01);
(Continued)

(58) Field of Classification Search
CPC .. A61F 2/142; A61F 2/148; A61F 2230/0023; A61F 2250/0097;
(Continued)

(56) References Cited

U.S. PATENT DOCUMENTS 5,152,786 A * 10/1992 Hanna ..................... A61F 2/145
606/166
5,964,748 A * 10/1999 Peyman .............. A61F 9/00812
606/17
(Continued)

FOREIGN PATENT DOCUMENTS

CN          1635115 A      7/2005
CN        106955372 A      7/2017
(Continued)

OTHER PUBLICATIONS

Mohit Parekh, Alessandro Ruzza, Stefano Ferrari, Massimo Busin, Diego Ponzin, Preloaded Tissues for Descemet Membrane Endothelial Keratoplasty, American Journal of Ophthalmology, vol. 166, 2016, pp. 120-125, ISSN 0002-9394, https://doi.org/10.1016/j.ajo.2016.03.048. (Year: 2016).*

(Continued)

*Primary Examiner* — Melanie R Tyson
*Assistant Examiner* — Yasniary De La Caridad Morales
(74) *Attorney, Agent, or Firm* — Mueting Raasch Group

(57) ABSTRACT

This disclosure describes a Descemet's membrane endothelial keratoplasty (DMEK) graft prepared using paired incisions; compositions including the incised DMEK graft; an injector including the incised DMEK graft; a viewing chamber including the incised DMEK graft, methods of preparing the incised DMEK graft; and methods of using the DMEK graft, the compositions, the injectors, and the viewing chambers including to facilitate placement of DMEK grafts during cornea transplant surgery.

37 Claims, 8 Drawing Sheets
(6 of 8 Drawing Sheet(s) Filed in Color)

(52) U.S. Cl.
CPC ....... *A61L 27/3808* (2013.01); *A61L 27/3886* (2013.01); *A61F 2/148* (2013.01); *A61F 2230/0023* (2013.01); *A61F 2250/0097* (2013.01); *A61L 2300/442* (2013.01); *A61L 2400/18* (2013.01); *A61L 2430/16* (2013.01)

(58) Field of Classification Search
CPC ............. A61L 27/3839; A61L 27/3691; A61L 27/3808; A61L 27/3886; A61L 2300/442; A61L 2400/18; A61L 2430/16; A61L 27/54

See application file for complete search history.

(56) References Cited

U.S. PATENT DOCUMENTS

| | | | |
|---|---|---|---|
| 7,347,876 | B2 | 3/2008 | Tsai |
| 8,889,415 | B2 | 11/2014 | Tsai |
| 10,041,865 | B2 | 8/2018 | Tran |
| 2010/0057093 | A1 | 3/2010 | Ide et al. |
| 2010/0256651 | A1 | 10/2010 | Jani et al. |
| 2011/0144579 | A1 | 6/2011 | Elton |
| 2014/0107778 | A1* | 4/2014 | Delhom Munoz ..... A61F 2/147 623/5.12 |
| 2014/0155871 | A1* | 6/2014 | Cumming ............... A61F 2/142 606/5 |
| 2014/0171956 | A1 | 6/2014 | Helmy et al. |
| 2014/0180221 | A1 | 6/2014 | Dias et al. |
| 2018/0106704 | A1* | 4/2018 | Tran ...................... A61F 2/0095 |
| 2018/0161149 | A1* | 6/2018 | Litvin ..................... A61F 2/142 |
| 2020/0060808 | A1* | 2/2020 | Chiang .................. A61F 2/142 |
| 2020/0338235 | A1 | 10/2020 | Honghan et al. |
| 2022/0183818 | A1 | 6/2022 | Binner et al. |
| 2022/0400655 | A1 | 12/2022 | Hou et al. |

FOREIGN PATENT DOCUMENTS

| | | |
|---|---|---|
| WO | WO 00/47040 A1 | 8/2000 |
| WO | WO 2008/155748 A2 | 12/2008 |
| WO | WO 2020/081934 A1 | 4/2020 |
| WO | WO 2022/241252 A1 | 11/2022 |

OTHER PUBLICATIONS

Alvarez et al., Reformulation of Fungizone by PEG-DSPE Micelles: Deaggregation and Detoxification of Amphotericin B. *Pharm Res* 33, 2098-2106 (2016).

Atallah et al., Limbal stem cell transplantation: current perspectives. Clin Ophthalmol 10, 593-602 (2016).

Badv et al., An omniphobic lubricant-infused coating produced by chemical vapor deposition of hydrophobic organosilanes attenuates clotting on catheter surfaces. *Sci Rep* 7, 11639 (2017).

Bhogal et al., Real-time assessment of corneal endothelial cell damage following graft preparation and donor insertion for DMEK. PLoS One 12, e0184824 (2017).

Brennan, "DMEK: New Insights, Emerging Advances" Review of Ophthalmology, Nov. 9, 2018; [retrieved Oct. 21, 2023]. Retrieved from the Internet: <URL: www.reviewofophthalmology.com/article/dmek-new-insights-emerging-advances> 9 pages.

Brothers et al., Association Between Fungal Contamination and Eye Bank-Prepared Endothelial Keratoplasty Tissue: Temperature-Dependent Risk Factors and Antifungal Supplementation of Optisol-Gentamicin and Streptomycin. *JAMA Ophthalmol* 135, 1184-1190 (2017).

Casaroli-Marano et al., Potential Role of Induced Pluripotent Stem Cells (IPSCs) for Cell-Based Therapy of the Ocular Surface. J Clin Med 4, 318-342 (2015).

Chandradoss et al., Surface Passivation for Single-molecule Protein Studies. J. Vis. Exp. (86), e50549, doi:10.3791/50549 (2014).

Chen et al., A new isolation method of human limbal progenitor cells by maintaining close association with their niche cells. Tissue Eng Part C Methods 17, 537-548 (2011).

Chen et al., Surface modification of silicate glass using 3-(mercaptopropyl)trimethoxysilane for thiol-ene polymerization. Langmuir 27, 13754-13761 (2011).

Chen et al., Transplantation of adult human corneal endothelium ex vivo: a morphologic study. Cornea 20, 731-737 (2001).

Connon et al., The variation in transparency of amniotic membrane used in ocular surface regeneration. Br J Ophthalmol 94, 1057-61 (2010).

De Araujo et al., Corneal stem cells and tissue engineering: current advances and future perspectives, *World J Stem Cells* 7, 806-814 (2015).

Dirisamer et al., Efficacy of descemet membrane endothelial keratoplasty: clinical outcome of 200 consecutive cases after a learning curve of 25 cases. Arch Ophthalmol 129, 1435-1443 (2011).

Downes et al., Cumulative Endothelial Cell Loss in Descemet Membrane Endothelial Keratoplasty Grafts From Preparation Through Insertion With Glass Injectors. Cornea 37, 698-704 (2018).

Droutsas et al., Visual Outcomes After Descemet Membrane Endothelial Keratoplasty Versus Descemet Stripping Automated Endothelial Keratoplasty-Comparison of Specific Matched Pairs. Cornea 35, 765-771 (2016).

Duncan et al., The Effect of Light Exposure on the Efficacy and Safety of Amphotericin B in Corneal Storage Media. JAMA Ophthalmol 134, 432-436 (2016).

Dunne et al., Human decellularized adipose tissue scaffold as a model for breast cancer cell growth and drug treatments. Biomaterials 35, 4940-4949 (2014).

EBAA-CS AAO 2018—ocular surface DM final, Cornea and Eye Banking Forum 2018, Chicago, IL, Oct. 28, 2018, 26 pages.

Edelstein SL, DeMatteo J, Stoeger CG, Macsai MS, Wang CH. Report of the Eye Bank Association of America medical review subcommittee on adverse reactions reported from 2007 to 2014. Cornea 2016;35:917-926.

Feizi et al., DMEK lenticule preparation using an air dissection technique: central versus peripheral injection. Eur J Ophthalmol 26, 6-11 (2016).

Feng et al., Review of alternative carrier materials for ocular surface reconstruction. Curr Eye Res 39, 541-552 (2014).

Gkana et al., Anti-adhesion and Anti-biofilm Potential of Organosilane Nanoparticles against Foodborne Pathogens. Front Microbiol 8, 1295 (2017).

Gloeckner et al., Monitoring of cell viability and cell growth in a hollow-fiber bioreactor by use of the dye Alamar Blue. J Immunol Methods 252, 131-138 (2001).

Gutermuth et al., Descemet's Membrane Biomimetic Microtopography Differentiates Human Mesenchymal Stem Cells Into Corneal Endothelial-Like Cells. Cornea 38, 110-119 (2019).

Haagdorens et al., Limbal Stem Cell Deficiency: Current Treatment Options and Emerging Therapies. Stem Cells Int 2016, 9798374 (2016).

Hansen, Apr. 23, 2019, "Video: Small relaxing incisions may allow easier DMEK surgery", available online [retrieved Apr. 25, 2019], 2 pages.

Hariya et al., Transparent, resilient human amniotic membrane laminates for corneal transplantation. Biomaterials 101, 76-85 (2016).

Heinzelmann et al., Influence of donor characteristics on descemet membrane endothelial keratoplasty. Cornea 33, 644-648 (2014).

Holland, Management of Limbal Stem Cell Deficiency: A Historical Perspective, Past, Present, and Future. Cornea 34 Suppl 10, S9-15 (2015).

Hou et al., Ex vivo expansion of limbal stem cells using Descemet's Membrane as a culture substrate. Invest Ophthalmol Vis Sci 60, 4128 (2019). Abstract presented at the 2019 ARVO Annual Meeting, Vancouver, Canada, Apr. 28-May 2, 2019.

Hou, Ex vivo expansion of limbal stem cells using Descemet's membrane as a culture substrate. E-poster presented at the 37th Congress of the European Society of Cataract and Refractive Surgeons (ESCRS), Sep. 14-18, 2019, Paris, France. 6 pages.

International Preliminary Report on Patentability for International Patent Application No. PCT/US2019/056938, Apr. 29, 2021, 9 pages.

(56) References Cited

OTHER PUBLICATIONS

International Search Report and Written Opinion for International Patent Application No. PCT/US2019/056938, Feb. 11, 2020, 11 pages.
International Search Report and Written Opinion for International Patent Application No. PCT/US2022/029249, mailed Aug. 11, 2022, 9 pages.
Janissen et al., Optimized straight forward procedure for covalent surface immobilization of different biomolecules for single molecule applications. Colloids Surf B Biointerfaces 71, 200-207 (2009).
Jinan 2019—ocular surface DM final, 12th International Symposium no New Ophthalmic Technology, Jinan, Shandong Province, China, Aug. 24, 2019, 34 pages.
Kabosova et al., Compositional differences between infant and adult human corneal basement membranes. Invest Ophthalmol Vis Sci 48, 4989-4999 (2007).
Khutoryanskaya et al., Multilayered hydrogel coatings covalently-linked to glass surfaces showing a potential to mimic mucosal tissues. Soft Matter, 2010, 6, 551-557.
Larson et al., A new, simple, nonradioactive, nontoxic in vitro assay to monitor corneal endothelial cell viability. Invest Ophthalmol Vis Sci 38, 1929-1933 (1997).
Layer et al., Efficacy and safety of antifungal additives in Optisol-GS corneal storage medium. JAMA Ophthalmol 132, 832-837 (2014).
Lohmeier et al., Viability of Descemet Membrane Endothelial Keratoplasty Grafts Folded in the Eye Bank. Cornea 37, 1474-1477 (2018).
LVG Patient Ready DMEK Press release page [online]. Lions Vision Gift, Boston, MA, 2019 [retrieved Oct. 21, 2023]. Retrieved from the Internet: <http://visiongift.org/wp-content/uploads/2019/02/LVG_DMEK_UPDATE_090717.pdf>, 1 page.
Maier et al., Influence of the difficulty of graft unfolding and attachment on the outcome in Descemet membrane endothelial keratoplasty. Graefes Arch Clin Exp Ophthalmol 253, 895-900 (2015).
Materne et al., Organosilane Technology in Coating Applications: Review and Perspectives. Dow Corning Corporation, Midland, MI; Copyright 2006, 2012; 16 pages.
Mittal K. Silanes and Other Coupling Agents, vol. 5. Boca Raton, FL: CRC Press; 2009.
Modabber et al., The role of novel DMEK graft shapes in facilitating intraoperative unscrolling. Graefes Arch Clin Exp Ophthalmol 256, 2385-2390 (2018).
Mohanty et al., Fabrication of scalable and structured tissue engineering scaffolds using water dissolvable sacrificial 3D printed moulds. Mater Sci Eng C Mater Biol Appl 55, 569-578 (2015).
Newman et al., Preloaded Descemet Membrane Endothelial Keratoplasty Donor Tissue: Surgical Technique and Early Clinical Results. Cornea 37, 981-986 (2018).
Parekh et al., Preloaded Tissues for Descemet Membrane Endothelial Keratoplasty. Am J Ophthalmol 166, 120-125 (2016).
Parekh et al., Preservation of Preloaded DMEK Lenticules in Dextran and Non-Dextran-Based Organ Culture Medium. J Ophthalmol 2016, 5830835 (2016).
Parekh et al., Standardizing Descemet Membrane Endothelial Keratoplasty Graft Preparation Method in the Eye Bank-Experience of 527 Descemet Membrane Endothelial Keratoplasty Tissues. Cornea 36, 1458-1466 (2017).
Park et al., Keratoplasty in the United States: A 10-Year Review from 2005 through 2014. Ophthalmology 122, 2432-2442 (2015).
Perrot et al. "A New Nondestructive Cytometric Assay Based on Resazurin Metabolism and an Organ Culture Model for the Assessment of Corneal Viability" Cytometry Part A, 2003; 55A:7-14.
Price et al., Evolution of endothelial keratoplasty. Cornea 32 Suppl 1, S28-32 (2013).
Proulx et al., Transplantation of a tissue-engineered corneal endothelium reconstructed on a devitalized carrier in the feline model. Invest Ophthalmol Vis Sci 50, 2686-2694 (2009).
Rennier et al., The role of death-associated protein kinase (DAPK) in endothelial apoptosis under fluid shear stress. Life Sci 93, 194-200 (2013).
Romano et al., Comparison of preservation and transportation protocols for preloaded Descemet membrane endothelial keratoplasty. Br J Ophthalmol 102, 549-555 (2018).
Sabater et al., Amniotic membrane use for management of corneal limbal stem cell deficiency. Curr Opin Ophthalmol 28, 363-369 (2017).
Sarnicola et al., Cannula-Assisted Technique to Unfold Grafts in Descemet Membrane Endothelial Keratoplasty. Cornea 38, 275-279 (2019).
Schallhorn et al., Quantification and Patterns of Endothelial Cell Loss Due to Eye Bank Preparation and Injector Method in Descemet Membrane Endothelial Keratoplasty Tissues. Cornea 35, 377-382 (2016).
Shafiq et al., Decellularized human cornea for reconstructing the corneal epithelium and anterior stroma. Tissue Eng Part C Methods 18, 340-348 (2012).
Sharifi et al., Isolation, culture, characterization and optimization of human corneal stem cells. Biocell 34, 53-55 (2010).
Silanikove and Shapiro, "Combined Assays for Lactose and Galactose by Enzymatic Reactions," in Dietary Sugars: Chemistry, Analysis, Function and Effects. *Preedy* (Ed.) RSC Publishing, The Royal Society of Chemistry: Cambridge, UK; 2012. Cover page, publisher's page, and pp. 395-404.
Singh et al., Science and Art of Cell-Based Ocular Surface Regeneration. Int Rev Cell Mol Biol 319, 45-106 (2015).
Suri et al., Human Platelet Lysate as a Replacement for Fetal Bovine Serum in Limbal Stem Cell Therapy. Curr Eye Res 41, 1266-1273 (2016).
Szurman, "Descemet Membrane Endothelial Keratoplasty: The Innovative System for Treating Endothelial Corneal Diseases" Product Brochure. Geuder AG, Heidelberg, Germany, 2017, 12 pages.
Terry, Endothelial keratoplasty: history, current state, and future directions. Cornea 25, 873-878 (2006).
Tran et al., Evaluation and Quality Assessment of Prestripped, Preloaded Descemet Membrane Endothelial Keratoplasty Grafts. Cornea 36, 484-490 (2017).
Tran et al., Measuring Endothelial Cell Loss on DMEK Grafts After Transplantation in Human Cadaveric Whole Eyes: Description of the Technique and Pilot Study. Cornea 37, 1075-1080 (2018).
Tsai et al., From stem cell niche environments to engineering of corneal epithelium tissue. Jpn J Ophthalmol 58, 111-119 (2014).
Wolle et al., Quantitative Analysis of Endothelial Cell Loss in Preloaded Descemet Membrane Endothelial Keratoplasty Grafts. Cornea 36, 1295-1301 (2017).
Zeidenweber et al., Prestained and Preloaded DMEK Grafts: An Evaluation of Tissue Quality and Stain Retention. Cornea 36, 1402-1407 (2017).
Zhang et al., An Ultra-thin Amniotic Membrane as Carrier in Corneal Epithelium Tissue-Engineering. Sci Rep 6, 21021 (2016).
Zhang et al., Comparison of Explant and Enzyme Digestion Methods for Ex Vivo Isolation of Limbal Epithelial Progenitor Cells. Curr Eye Res 41, 318-325 (2016).
Zhao et al., Systematic review and meta-analysis on transplantation of ex vivo cultivated limbal epithelial stem cell on amniotic membrane in limbal stem cell deficiency. Cornea 34, 592-600 (2015).
Zhou et al., Noninvasive real-time monitoring by alamarBlue((R)) during in vitro culture of three-dimensional tissue-engineered bone constructs. Tissue Eng Part C Methods 19, 720-729 (2013).
DeMill et al., Frozen, Pre-stripped Descemet Membrane Endothelial Keratoplasty (DMEK) Grafts for Surgical Training, International Journal of Eye Banking, 5(2) (Jul. 2017).
James et al. "The Potential for Eye Bank Limbal Rings to Generate Cultured Corneal Epithelial Allografts." Cornea, vol. 20(5), 2001, pp. 488-494. (Year: 2001).
Mikhailova et al. "Human pluripotent stem cell-derived limbal epithelial stem cells on bioengineered matrices for corneal reconstruction." Experimental Eye Research, vol. 146 (2016) pp. 26-34. (Year: 2016).

(56) References Cited

OTHER PUBLICATIONS

Regnier et al., Eye bank prepared versus surgeon cut endothelial graft tissue for Descemet membrane endothelial keratoplasty: An observational study. Medicine (Baltimore) 96, e6885 (2017).
Guindolet et al., "Storage of Porcine Cornea in an Innovative Bioreactor" Investigative Ophthalmology & Visual Science, Nov. 2017; 58(13): 5907-5917.

* cited by examiner

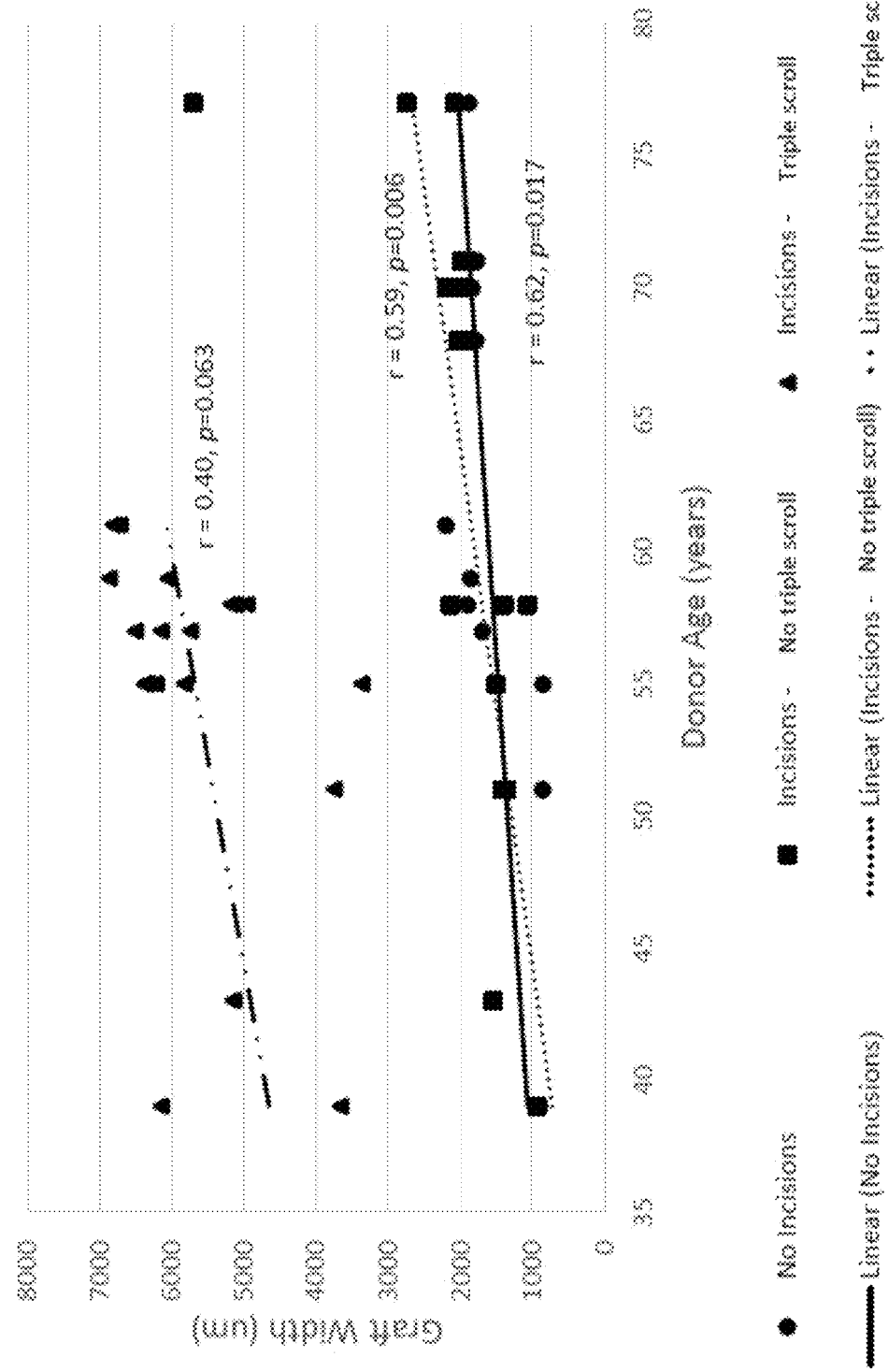

INCISED DESCEMET'S MEMBRANE AND METHODS OF MAKING AND USING

CONTINUING APPLICATION DATA

This application claims the benefit of U.S. Provisional Application Ser. No. 62/838,986, filed Apr. 26, 2019, which is incorporated by reference herein.

BACKGROUND

Endothelial keratoplasty (EK), a cornea transplant technique, is the preferred way to restore vision when the inner cell layer of the cornea, known as endothelium, stops working properly from Fuchs' dystrophy, bullous keratopathy, iridocorneal endothelial (ICE) syndrome, or other endothelial disorders. Endothelial keratoplasty selectively replaces only the diseased posterior layers of the cornea, leaving healthy areas intact. The two most common forms of endothelial keratoplasty are Descemet's Stripping Endothelial Keratoplasty (DSEK) and Descemet's Membrane Endothelial Keratoplasty (DMEK).

Descemet's membrane endothelial keratoplasty (DMEK) is increasingly becoming the preferred treatment for corneal endothelial failure. (Terry *Cornea* 2006; 25:873.) Unlike Descemet's stripping endothelial keratoplasty (DSEK), DMEK provides an exact anatomical replacement of diseased endothelium. (Price et al. *Cornea*. 2013; 32 Suppl 1:S28-32.) DMEK has further been shown to result in better post-operative vision acuity, faster visual rehabilitation, and lower rejection rates when compared to DSEK. (Droutsas et al. *Cornea.* 2016; 35:765-771.) Despite these advantages, surgeon adoption of DMEK has still lagged behind DSEK due to the steep learning curve for surgeons and the technical challenges associated with DMEK. (Dirisamer et al. *Arch Ophthalmol.* 2011; 129:1435-1443.) Thus, improvements to DMEK graft design and DMEK transplant technique that facilitate the surgery would be beneficial.

SUMMARY OF THE INVENTION

This disclosure describes a DMEK graft prepared using paired incisions; compositions including the incised DMEK graft; an injector including the incised DMEK graft; methods of preparing the incised DMEK graft; and methods of using the DMEK graft, the compositions, and the injectors including to facilitate placement of DMEK grafts during cornea transplant surgery.

In one aspect, this disclosure describes a composition for corneal transplantation including: a DMEK graft including two incisions; wherein the DMEK graft comprises Descemet's membrane and corneal endothelial cells; and wherein the two incisions are placed in a range of 105 degrees to 135 degrees apart from each other, relative to a geometric center of the DMEK graft.

In another aspect, this disclosure describes a method that includes providing a DMEK graft including Descemet's membrane and corneal endothelial cells and making two incisions to the DMEK graft to form an incised DMEK graft, wherein the two incisions are placed in a range of 105 degrees to 135 degrees apart from each other, relative to a geometric center of the DMEK graft.

In a further aspect, this disclosure describes a method that includes injecting an incised DMEK graft into the anterior chamber of an eye. In yet another aspect, this disclosure describes an injector including an incised DMEK graft. In an additional aspect, this disclosure describes a viewing chamber including an injector that includes an incised DMEK graft. The incised DMEK graft includes Descemet's membrane and corneal endothelial cells; and the incised DMEK graft includes two incisions, the two incisions placed in a range of 105 degrees to 135 degrees apart from each other, relative to a geometric center of the DMEK graft.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

All headings are for the convenience of the reader and should not be used to limit the meaning of the text that follows the heading, unless so specified.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The patent or application file contains drawings and photographs executed in color. Copies of this patent or patent application publication with color drawings and photographs will be provided by the Office upon request and payment of the necessary fee.

FIG. 3A: The graft is injected into the anterior chamber. As shown in FIG. 3B, at this stage, the graft curls with Descemet's Membrane (D) on the inside and the endothelium (E) on the outside. FIG. 3C: Balanced salt solution is injected to begin orienting and unfurling the graft.

FIG. 3D: The graft is unfurled by gently tapping the top of the cornea with a cannula. FIG. 3E: The graft is centered by tapping the outer corneal surface. FIG. 3F: The unscrolled graft is positioned against the cornea by a gas bubble (for example, sulfur hexafluoride).

FIG. 7 shows regression analysis comparing graft width to donor age. Pre-incision graft width increased with increasing donor age. Post-incision, only grafts that remained single or double scrolls (failed to form triple scrolls) showed a similar statistically significant increase in graft width with increasing donor age. Grafts that formed triple scrolls were significantly wider than single or double scrolls and the width did not change significantly with donor age.

DETAILED DESCRIPTION OF ILLUSTRATIVE EMBODIMENTS

This disclosure describes a DMEK graft prepared using paired incisions; compositions including the incised DMEK graft; an injector including the incised DMEK graft; methods of preparing the incised DMEK graft; and methods of using the DMEK graft, the compositions, and the injectors, including to facilitate placement of DMEK grafts during cornea transplant surgery.

Corneal Anatomy and the Role of Corneal Endothelium

Figure 1:
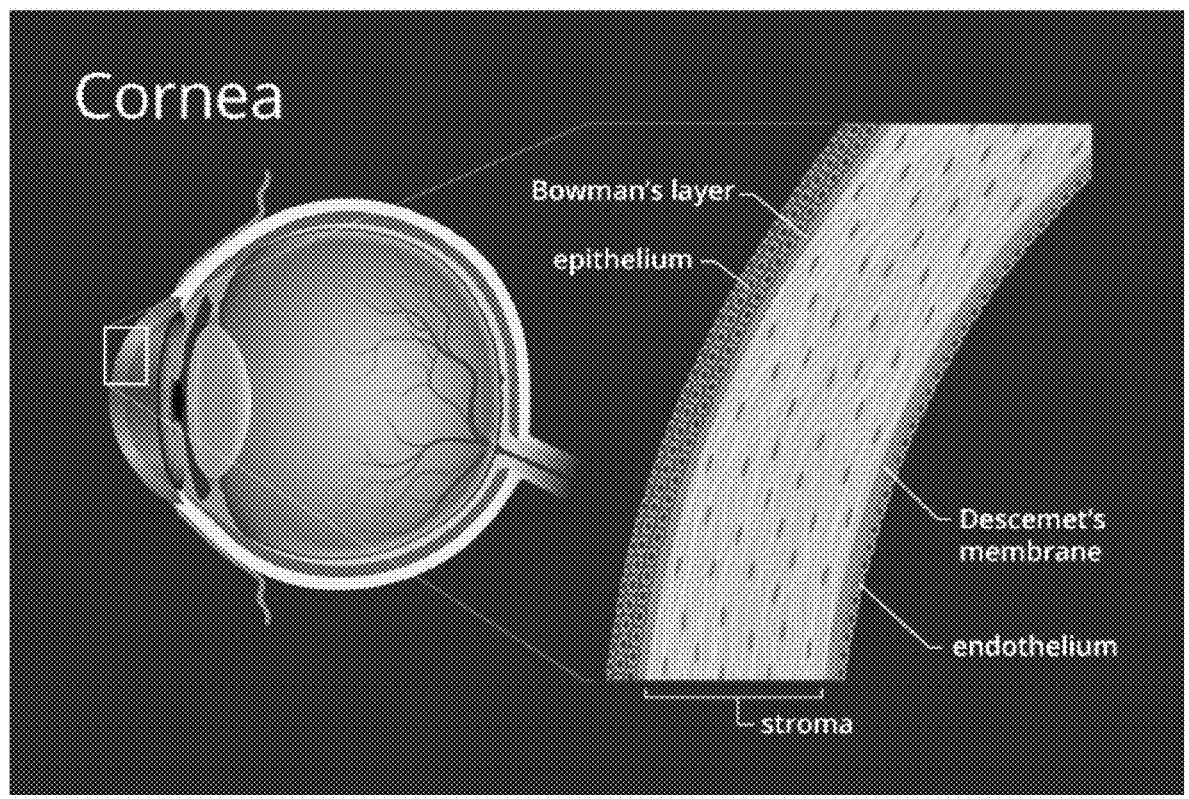
FIG. 1 shows a schematic cross-sectional view of a cornea and identifies the different layers of the cornea.
Figure 2A:
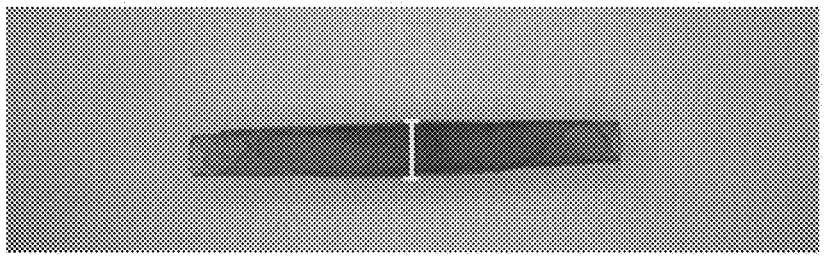
FIG. 2A shows an exemplary Descemet's Membrane Endothelial Keratoplasty (DMEK) graft in a single scroll conformation.
Figure 2B:
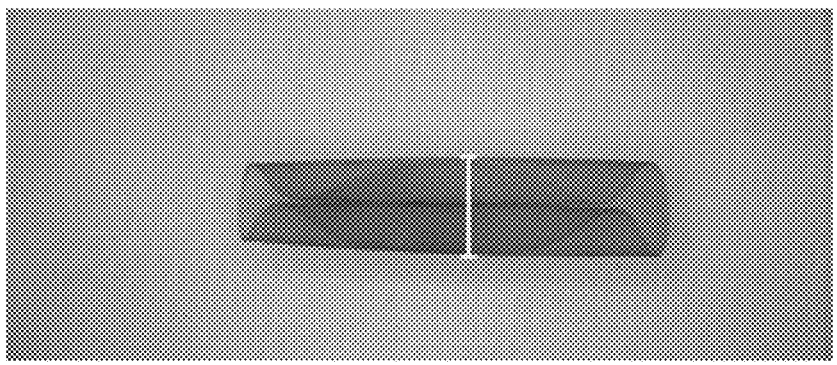
FIG. 2B shows an exemplary DMEK graft in a double scroll conformation. The bars indicate the graft width.
Figure 2C:
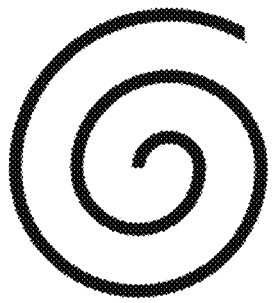
FIG. 2C shows a schematic of the cross-sectional view of a DMEK graft in a single scroll conformation.
Figure 2D:
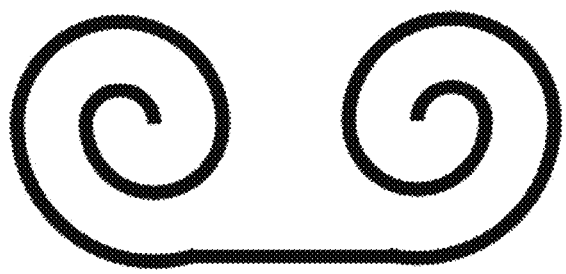
FIG. 2D shows a schematic of the cross-sectional view of a DMEK graft in a double scroll conformation.
Figure 3A:
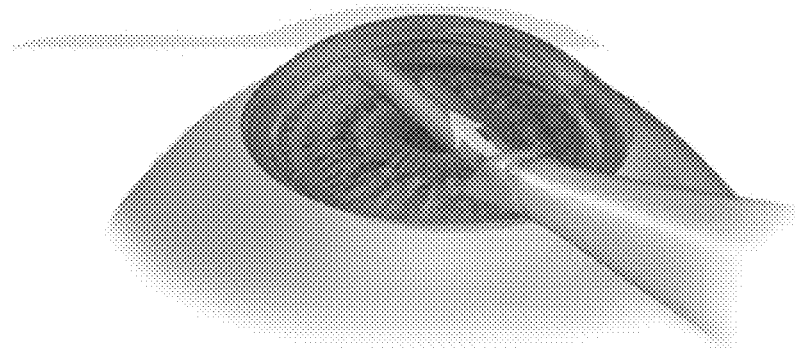
FIG. 3A-FIG. 3F show the steps of a Descemet's Membrane Endothelial Keratoplasty (DMEK) procedure.
Figure 3B:
Figure 3C:
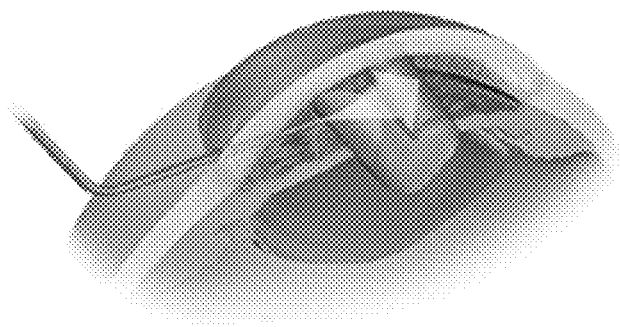
Figure 3D:
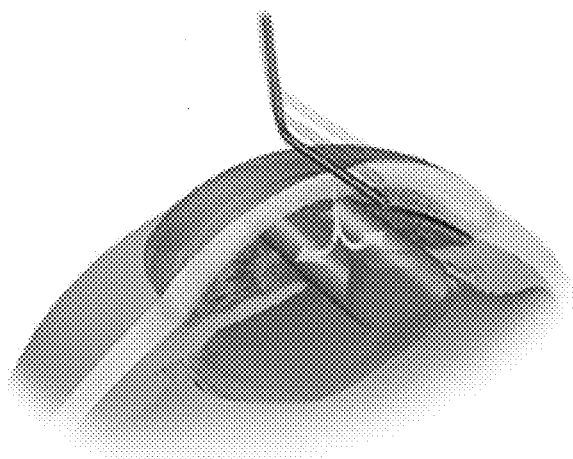
Figure 3E:
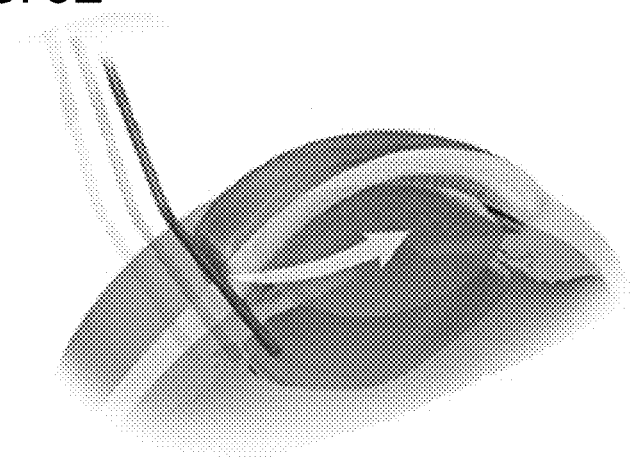
Figure 3F:
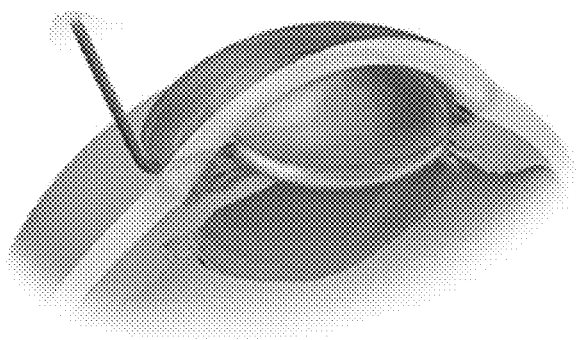

The cornea is the clear shield in front of the eye that is responsible for the majority of the focusing power of the eye. The cornea has several layers, including an epithelium, stroma, Descemet's membrane, and endothelium, as shown in FIG. 1. Descemet's membrane and the endothelium that covers Descemet's membrane constitute the two most posterior layers of the cornea.

Corneal endothelium serves a critical role in eye health. Individual endothelial cells pump water out of the cornea. Without functional endothelial cells, the cornea swells from hydrostatic pressure, which forces fluid from inside the eye into the cornea. This fluid buildup leads to opacification and the formation of painful blisters on the cornea. The most common indication for corneal transplantation is dysfunction or loss of endothelial cells. Such dysfunction or loss of endothelial cells may result from Fuchs' dystrophy, bullous keratopathy, iridocorneal endothelial (ICE) syndrome, or other endothelial disorders.

Corneal endothelial cells do not regenerate and replace themselves; once damaged, the only treatment is transplantation of new endothelial cells. Endothelial keratoplasty (EK) selectively replaces only the diseased posterior layers of the cornea, leaving healthy layers of the cornea intact. The two most common forms of endothelial keratoplasty are Descemet's Stripping Endothelial Keratoplasty (DSEK) and Descemet's Membrane Endothelial Keratoplasty (DMEK).

Current State of Endothelial Keratoplasty (EK)

During Descemet's membrane endothelial keratoplasty (DMEK) or Descemet's stripping endothelial keratoplasty (DSEK), a patient's existing (often diseased or damaged) corneal endothelium and Descemet's membrane are removed and replaced with a corneal graft. A DMEK graft includes a healthy Descemet's membrane with endothelial cells attached. A DSEK graft includes posterior corneal stroma, Descemet's membrane, and endothelium. Thus, unlike DSEK, DMEK provides an exact anatomical replacement of diseased endothelium. (Price et al. *Cornea*. 2013; 32 Suppl 1:S28-32.) DMEK has further been shown to result in better post-operative vision acuity, faster visual rehabilitation, and lower rejection rates when compared to DSEK. (Droutsas et al. *Cornea*. 2016; 35:765-771.)

Performing DMEK is, however, more technically challenging than DSEK due to the thinness of the graft and its natural tendency to scroll. The graft has a natural tendency to form a single scroll or a double scroll. As shown in FIG. 2, a single scroll is formed when the graft wraps around itself around a single axis, and a double scroll is formed when the two halves of the graft wrap around two parallel axes. Intraoperatively, the graft must be unscrolled, oriented, and centered within the anterior chamber of the eye. This procedure often requires extensive intraoperative manipulation which can lead to unpredictable operating times, increased endothelial cell loss, and higher rates of post-operative graft detachment compared to Descemet's stripping endothelial keratoplasty (DSEK). (Maier et al. *Graefes Arch Clin Exp Ophthalmol*. 2015; 253:895-900.)

In DMEK, damaged endothelium and Descemet's membrane are stripped from the back of the patient's cornea. Healthy Descemet's membrane with endothelial cells attached from a donor cornea (also referred to as a DMEK graft) is then inserted to the recipient eye using an injector. Insertion of the DMEK graft is further described below and in the figure legend of FIG. 3. Upon injection into the recipient eye, the DMEK graft always curls or scrolls, and it always scrolls with endothelium on the outside of the scroll. After injection of the graft into the eye, the graft is unscrolled and centered without any further touching of the graft (using jets of fluid or external tapping). Once the graft is appropriately positioned, an air bubble is used to position the graft against the recipient cornea. After 24 hours to 48 hours, the DMEK graft adheres to the recipient cornea and the air bubble dissipates. For the surgery to be successful, the endothelial cells on the DMEK graft must survive the transplantation. The overall number of cells that survive will determine how quickly the graft will start working to clear the vision and how long the graft will last before it fails (even after surgery, the endothelial cells will die slowly over time and when they have all died, the recipient will need another transplant to maintain vision).

Despite multiple refinements in DMEK surgical techniques, intraoperative unscrolling remains one of the most difficult aspects of DMEK surgery. (Sarnicola et al. *Cornea* 2019; 38:275.) In particular, surgeons must learn a variety of maneuvers to unscroll and center a graft without traumatizing the tissue of the graft. The most popular techniques in use at the time of the invention included tapping maneuvers on the external cornea to create fluid waves in the anterior chamber or using jets of balanced salt solution injected directly into the eye to unscroll the graft. (See, e.g., Straiko. May 7, 2013. "DMEK Techniques and Tips", available online at www.youtube.com/watch?v=NuC7ZjHGICc.) While a few highly talented and experienced surgeons have been able to show consistent results with mastery of these techniques, the difficulty most surgeons have with these techniques has limited overall adoption of DMEK as a surgery. Even for highly experienced surgeons, the difficulty with unscrolling still makes for unpredictable surgical times and a higher rate of graft detachment in DMEK than in DSEK.

Moreover, at the time of the invention, tissues from younger donors (for example, up to of 65 years of age) and especially from very young donors (for example, up to of 50 years of age) were routinely avoided in DMEK surgery, even by experienced surgeons, since tissue from younger donors tend to scroll more tightly. (Heinzelmann et al. *Cornea*. 2014; 33:644-648.) This scrolling precluded the use of very young donor tissues which, on average, have more endothelial cells and take longer to fail. Furthermore, increased difficulty in graft unfolding has specifically been associated with higher rates of post-operative graft detachments and endothelial cell loss. (Maier et al. *Graefes Arch Clin Exp Ophthalmol*. 2015; 253:895-900.)

Methods to facilitate unscrolling of the graft are important for expanding surgeon adoption and improving patient outcomes with DMEK.

Previous Efforts to Facilitate Unscrolling of the DMEK Graft

Others have attempted to address the challenge of unscrolling tightly wound scrolls with limited success. For example, Sarnicola et al. describe a cannula-based surgical tool to aid unrolling in the eye. (Sarnicola et al. *Cornea*. 2019; 38:275.) The cannula is placed inside the scrolled graft and has side ports that eject jets of fluid out from the inside of the scroll, opening the graft temporarily. While the graft maintains a favorable partially-open conformation while the fluid pressure is applied, the graft often scrolls up again as soon as fluid pressure stops. The surgeon must, therefore, learn another set of non-facile surgical maneuvers to catch the scroll in its partially open conformation. Although it is commercially available, the cannula has not been widely adopted.

Modabber et al. tested the impact of adding four equally spaced incisions to a DMEK graft and reported no conformational change or increase in scrolled graft width submerged in a balanced salt solution (BSS). Instead of forming a quadrangular fold, the graft continued to scroll naturally. (Modabber et al. *Graefe's Archive for Clinical and Experimental Ophthalmology* 2018; 256: 2385-2390.) Modabber et al. tried several other shape alterations that significantly reduced the number of viable cells transplanted without significantly widening the scroll. (Id.) Furthermore, Modabber et al. did not demonstrate the effect of the proposed alterations on surgery times. (Id.)

Incised DMEK Graft

In one aspect, this disclosure describes a DMEK graft including two incisions, wherein the DMEK graft includes Descemet's membrane and corneal endothelial cells. In contrast to a DSEK graft, the DMEK graft does not include posterior corneal stroma. In a further aspect, this disclosure describes a composition including the incised DMEK graft.

In some embodiments, the DMEK graft is up to 30 microns thick, up to 25 microns thick, up to 20 microns thick, up to 15 microns thick, or up to 10 microns thick. In some embodiments, the DMEK graft is at least 1 micron thick, at least 5 microns thick, or at least 10 microns thick. In an exemplary embodiment, the DMEK graft is in a range of 10 microns to 25 microns thick.

The DMEK graft typically has a shape like that of a contact lens, with a single circular graft edge, as shown in exemplary embodiments in FIG. 4A-FIG. 4D. The graft may, however, have a single elliptical or ovular graft edge, as shown in an exemplary embodiment in FIG. 4E. Alternatively, the graft may not have a single graft edge, but in such embodiments, it is anticipated that the overall shape of the graft is still mostly circular, elliptical, or ovular, and any modifications that cause the graft edge not to be a single edge do not significantly affect the overall shape of the graft.

In some embodiments, the incisions are radial incisions, that is, the incisions follow lines that point to a common center. The radial incisions may extend at least 0.3 mm, at least 0.4 mm, at least 0.5 mm, at least 0.6 mm, at least 0.7 mm, at least 0.8 mm, at least 0.9 mm, at least 1 mm, at least 1.1 mm, at least 1.2 mm, at least 1.3 mm, at least 1.4 mm, at least 1.5 mm towards the geometric center of the graft from the graft edge. In some embodiments, the radial incisions extend up to 0.4 mm, up to 0.5 mm, up to 0.6 mm, up to 0.7 mm, up to 0.8 mm, up to 0.9 mm, up to 1 mm, up to 1.1 mm, up to 1.2 mm, up to 1.3 mm, up to 1.4 mm, up to 1.5 mm, up to 1.6 mm, up 1.7 mm, up to 1.8 mm, up to 1.9 mm, or up to 2 mm towards the geometric center of the graft from the graft edge. For example, in some embodiments, the radial incision may extend at least 0.3 mm and up to 2 mm towards the geometric center of the graft from the graft edge. In another exemplary embodiment, the radial incision may extend at least 0.5 mm and up to 1.6 mm towards the geometric center of the graft from the graft edge.

In some embodiments, the incisions may extend along vectors formed by two sides of an isosceles triangle. (See, e.g. FIG. 4E.) In some embodiments, when the incisions extend along vectors formed by two sides of an isosceles triangle, the incisions extend along the vectors formed of the two equal length sides of the isosceles triangle. In some embodiments, the incisions may extend along vectors formed by two sides of an equilateral triangle. (See, e.g., FIG. 4C-FIG. 4D.) The incisions may extend at least 0.3 mm, at least 0.4 mm, at least 0.5 mm, at least 0.6 mm, at least 0.7 mm, at least 0.8 mm, at least 0.9 mm, at least 1 mm, at least 1.1 mm, at least 1.2 mm, at least 1.3 mm, at least 1.4 mm, at least 1.5 mm from the edge of the graft. In some embodiments, the incisions extend up to 0.4 mm, up to 0.5 mm, up to 0.6 mm, up to 0.7 mm, up to 0.8 mm, up to 0.9 mm, up to 1 mm, up to 1.1 mm, up to 1.2 mm, up to 1.3 mm, up to 1.4 mm, up to 1.5 mm, up to 1.6 mm, up 1.7 mm, up to 1.8 mm, up to 1.9 mm, or up to 2 mm from the edge of the graft. For example, in some embodiments, each incision may extend at least 0.3 mm and up to 2 mm from the edge of the graft along a vector formed one of the two equal length sides of an isosceles triangle or one of the sides of an equilateral triangle. In another exemplary embodiment, each incision may extend at least 0.5 mm and up to 1.6 mm from the edge of the graft along a vector formed one of the two equal length sides of an isosceles triangle or one of the sides of an equilateral triangle.

The distance between the incisions (in degrees) is measured relative to the geometric center of a DMEK graft. Although most DMEK grafts are circular—and the geometric center of the graft would be the center of the circle—some DMEK grafts have an elliptical or ovular shape.

Figure 4B:
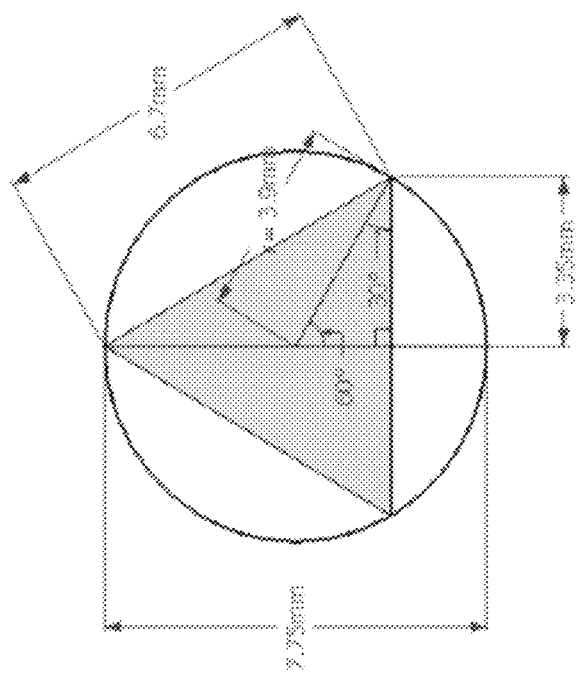
FIG. 4B shows a schematic demonstrating that for a 7.75 mm graft, maximum triple scroll width is 6.7 mm.
Figure 4A:
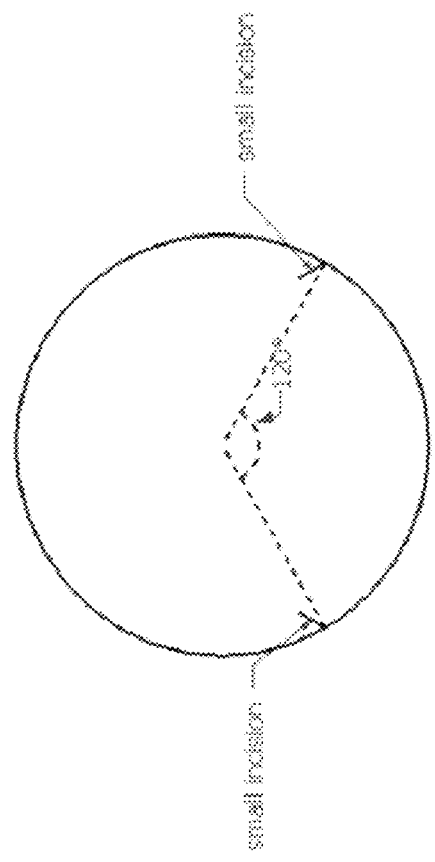
FIG. 4A shows a schematic demonstrating that 120° of separation between pair incisions, the distance (in degrees), measured relative to the geometric center of the DMEK graft, maximizes the width of a potential DMEK triple scroll.
Figure 4E:
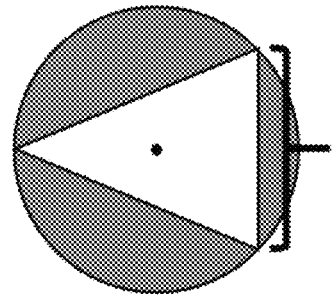
FIG. 4E shows a schematic showing a circumcircle of an isosceles triangle, the center of the circumcircle is indicated by a black dot, and a bracket identifies width of the graft (that is, the shortest side of the triangle) when the graft is viewed en face.

In some embodiments, the incisions are placed at least 45 degrees, at least 50 degrees, at least 55 degrees, at least 60 degrees, at least 65 degrees, at least 70 degrees, at least 75 degrees, at least 80 degrees, at least 85 degrees, at least 90 degrees, at least 95 degrees, at least 100 degrees, at least 105 degrees, at least 110 degrees, at least 115 degrees, or at least 120 degrees apart from each other. In some embodiments, the incisions are placed up to 110 degrees, up to 115 degrees, up to 120 degrees, up to 125 degrees, up to 130 degrees, up to 135 degrees, up to 140 degrees, up to 145 degrees, up to 150 degrees, up to 155 degrees, up to 160 degrees, up to 165 degrees, up to 170 degrees, up to 175 degrees, or up to 180 degrees apart from each other. For example, in some embodiments, the incisions are placed at a distance apart from each other in a range of 80 degrees to 160 degrees. In some embodiments, the incisions are placed at a distance apart from each other in a range of 100 degrees to 140 degrees. In some embodiments, the incisions are placed at a distance apart from each other in a range of 105 degrees to 135 degrees. In some embodiments, the incisions are placed at a distance apart from each other in a range of 110 degrees to 130 degrees. In an exemplary embodiment, the incisions are placed at a distance apart from each other of 120 degrees, as shown in FIG. 4A. In another exemplary embodiment, the incisions are placed at a distance apart from each other of less than 120 degrees, as shown in FIG. 4E.

As further described below, when the incisions are placed 120 degrees apart from each other and forceps are used to grasp the DMEK graft, the forceps may contact the graft at a point 120 degrees from either incision point.

In some embodiments, the DMEK graft may include a third incision. However, the DMEK graft does not contain more than three incisions.

In some embodiments, a third incision in the DMEK graft (including, for example, at a point that would form the third vertex of a triangle) is avoided because of the risk of tearing. A third incision at the remaining apex of the triangle would align the incision to the tensile force associated with separating the graft from the corneoscleral disc, increasing the risk that adding another incision would result in an elongated radial tear (including, for example, when the graft is lifted with forceps). Thus, in some embodiments, it is preferred that the graft includes only two incisions. In a safety study when two incisions were used, there was no increased risk of tissue loss due to unintentional tears extending from the incisions during graft preparation or insertion. Moreover, the use of paired incisions in the DMEK graft may significantly reduce the learning curve and surgical times for a novice DMEK surgeon and extend the potential age range of donors.

The incisions in the DMEK graft induce a change in the conformation of the DMEK graft. The incisions in the DMEK graft form two vertices of a triangle (as shown in an exemplary embodiment in FIG. 4B). In contrast to a non-incised DMEK graft—which forms a scroll conformation (as shown in FIG. 2, FIG. 5A, FIG. 5B, and FIG. 6A)—the DMEK graft including two incisions forms triple scroll conformation (also referred to herein simply as a "triple scroll," as shown in exemplary images in FIG. 5C, FIG. 6C, FIG. 6E, and FIG. 6G), having three corners. In some embodiments, the DMEK graft including two incisions forms a graft conformation having three sides, three sides being approximately equal in length.

In a triple scroll conformation, an incised DMEK graft forms a circumcircle of a triangle with the triangle forming a mostly planar region, and the segments of the circle outside the triangle folding towards the center of the circumcircle. (See FIG. 4C, FIG. 5C, FIG. 6C, FIG. 6E, and FIG. 6G). An incised DMEK graft in a triple scroll conformation has three scrolling axes; and the graft edge scrolls around the three axes until they prevent one another from scrolling further.

A person having skill in the art will recognize that the triple scroll conformation should not be confused with a "trifolded" graft that forms a conformation like a trifold wallet (see, e.g., Romano et al. *Br. J. Opthamology* 2018; 102(4):549-555).

Figure 4D:
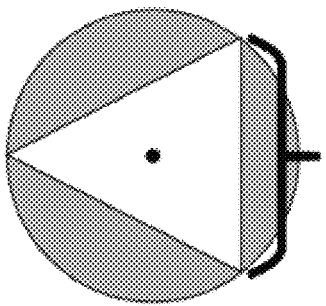
FIG. 4D shows the schematic of FIG. 4C where a bracket identifies the width of the graft when the graft is viewed en face. (When a perfect equilateral triangle is formed, each side of the triangle will be the width of the graft.)
Figure 4C:
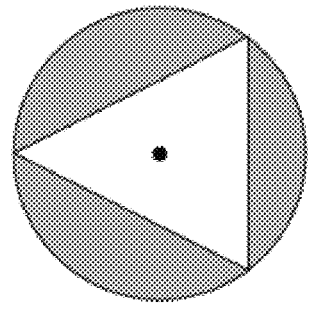
FIG. 4C shows a schematic showing a circumcircle of an equilateral triangle where the segments of the circle outside the triangle are shaded in gray and the center of the circumcircle is indicated by a black dot.

In an exemplary embodiment, when the incisions are placed 120 degrees apart from each other, as shown in FIG. 4A, the graft will form an equilateral triangle, as shown in FIG. 4C. When the incisions are placed more than 120 degrees apart from each other or less than 120 degrees apart from each other, the graft will form an isosceles triangle, as shown in an exemplary embodiment in FIG. 4E.

Figure 5A:
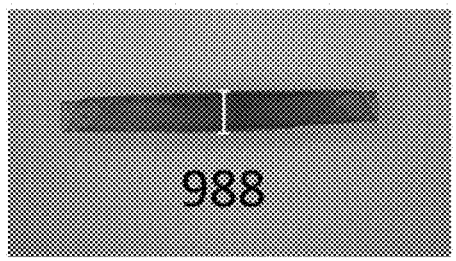
FIG. 5A shows an exemplary image of a DMEK graft in a single scroll conformation.
Figure 5B:
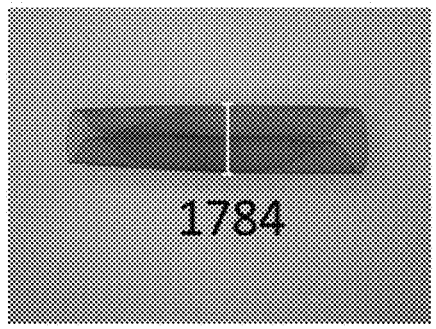
FIG. 5B shows a DMEK graft in a double scroll conformation.
Figure 5C:
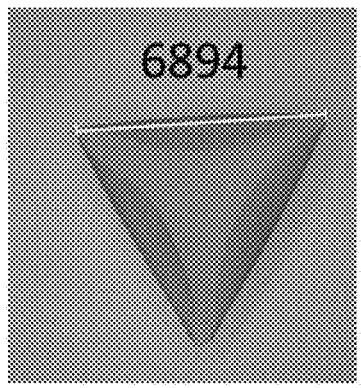
FIG. 5C shows a DMEK graft in a triple scroll conformation. In each image, width (measured in μm) of the graft at the location marked by the line is indicated. When the DMEK graft forms an equilateral triangle in the triple scroll configuration, each side of the triangle will be the width of the graft; when the DMEK graft forms an isosceles triangle in the triple scroll configuration, the shortest side of the triangle is considered to be the width of the graft.

As further described in Example 1, the use of the paired incisions in the DMEK graft results in a DMEK graft that, in a triple scroll conformation, is wider than a non-incised graft in a single scroll or double scroll conformation. As shown in an exemplary image in FIG. 5A, a single scroll (formed when graft wraps around itself around a single axis) conformation is the narrowest configuration, with the representative graft shown has a width of 988 µm. As shown in FIG. 5B, a double scroll conformation (formed when the two halves of the graft wrap around two parallel axes) are generally wider than a single scroll conformation, with the representative graft shown having a width of 1784 µm. In contrast, as shown in FIG. 5C, a graft in a triple scroll conformation has a planar region in the center and is the widest of all the scrolled graft configurations, with the representative graft having a width of 6894 µm.

As noted above, the incised DMEK graft forms a circumcircle of a triangle with the triangle forming a mostly planar region, and, in a scrolled conformation, the segments of the circle outside the triangle fold towards the center of the circumcircle. (See FIG. 4C) The measured width of the incised DMEK graft in the triple scrolled conformation reflects the shortest side of the triangle when the graft is viewed en face (that is, when looking down on the central planar region of the triple scroll), as shown in FIG. 4D and FIG. 4E. In some embodiments, the incised DMEK graft is at least 2000 microns wide, at least 2500 microns wide, at least 3000 microns wide, at least 3500 microns wide, at least 3600 microns wide, at least 3700 microns wide, at least 3800 microns wide, at least 3900 microns wide, at least 4000 microns wide, at least 4100 microns wide, at least 4200 microns wide, at least 4300 microns wide, at least 4500 microns wide at least 5000 microns wide, at least 5500 microns wide, at least 6000 microns wide, at least 6500 microns wide, at least 6600 microns wide, at least 6700 microns wide, at least 6800 microns wide, at least 6900 microns wide, at least 7000 microns wide, at least 7100 microns wide, at least 7200 microns wide, or at least 7300 microns wide, as measured in a stable submerged conformation. As used herein, a graft in a "stable submerged conformation" refers to a DMEK graft has assumed a stable conformation while completely submerged in a balanced salt solution, corneal storage media, or aqueous humor. In some embodiments, a DMEK graft has assumed a stable conformation is DMEK graft that has been submerged in a balanced salt solution, corneal storage media, or aqueous humor for at least 60 seconds. Exemplary corneal storage medias include, for example, OptiSol-GS (Bausch & Lomb), LIFE4° C. (Numedis, Isanti, MN).

In contrast, a scrolled DMEK graft without the paired incisions in a stable submerged conformation is typically less than 2000 microns wide.

The maximum width of an unscrolled DMEK graft is typically the width of the trephine block used to form the DMEK graft or, for example, up to 7000 microns, up to 7250 microns, up to 7500 microns, up to 7750 microns, up to 8000 microns, up to 8500 microns, up to 9000 microns, or up to 9500 microns.

In some embodiments, the incised DMEK graft may include tissue isolated from a donor having an age of up to 90 years, up to 85 years, up to 80 years, up to 75 years, up to 70 years, up to 65 years, up to 60 years, up to 55 years, or up to 50 years. In some embodiments, the incised DMEK graft may include tissue isolated from a donor having an age of at least 20 years, at least 30 years, at least 40 years, at least 45 years, at least 50 years, at least 55 years, at least 60 years, at least 65 years. As noted above, the use of an incised DMEK graft may extend the potential age range of donors. Use of an incised graft permit the use of grafts from younger donors which have traditionally been avoided because of their tendency to form tightly scrolled grafts (see FIG. 7) which are more difficult to unscroll and position during surgical insertion.

In some embodiments, the incised DMEK graft may be excised completely from the rest of the cornea (including the corneolimbal ring) including, for example, by trephination.

In some embodiments, the incised DMEK graft may be stained with a dye including, for example, trypan blue.

In some embodiments, the incised DMEK graft may include an orientation mark including, for example, a gentian violet posterior/anterior orientation mark In some embodiments, a composition including the incised DMEK graft further includes a pharmaceutically acceptable carrier. Any suitable pharmaceutically acceptable carrier may be used including, for example, a buffer, a cell culture media, a cell storage media, an excipient, a diluent, a solvent, an accessory ingredient, and/or a stabilizer. In some embodiments, a media may include a corneal storage media. Exemplary corneal storage medias include, for example, OptiSol-GS (Bausch & Lomb), LIFE4° C. (Numedis, Isanti, MN). In some embodiments, the composition is preferably sterile, fluid, and stable under the conditions of manufacture and storage.

Injector Including a DMEK Graft

In another aspect, this disclosure describes an injector including an incised DMEK graft as described herein.

In some embodiments, the injector includes a glass surface including, for example, a Straiko modified Jones tube (available from Gunther Weiss Scientific Glassblowing Co., Inc., Portland, OR), a pipette as included in a DMEK Disposable Surgical Set (available from DORC, the Netherlands), or a DMEK Cartridge (available from Geuder, Heidelberg, Germany). In some embodiments, the injector includes a plastic surface. In some embodiments, the injector includes a commercially available injector including, for example, an Endoject injector (available from Medicel, Altenrhein, Switzerland) or a DMEK EndoGlide (available from Network Medical, North Yorkshire, UK).

In some embodiments, the injector further includes a pharmaceutically acceptable carrier. Any suitable pharmaceutically acceptable carrier may be used including, for example, a buffer, a cell culture media, a cell storage media, an excipient, a diluent, a solvent, an accessory ingredient, and/or a stabilizer. In some embodiments, a media may include a corneal storage media. Exemplary corneal storage medias include, for example, OptiSol-GS (Bausch & Lomb), LIFE4° C. (Numedis, Isanti, MN).

In some embodiments, the incised DMEK graft may exclude any corneolimbal ring tissue.

In some embodiments, the incised DMEK graft included in the injector may preferably be stained with a dye including, for example, trypan blue.

In some embodiments, the incised DMEK graft included in the injector may include an orientation mark including, for example, a gentian violet posterior/anterior orientation mark.

Viewing Chamber Including a DMEK Graft

In another aspect, this disclosure describes a viewing chamber including an incised DMEK graft. In some embodiments, the incised DMEK graft in the viewing chamber may be disposed in an injector.

Any suitable viewing chamber may be used. Exemplary viewing chambers include corneal viewing chambers available from Bausch & Lomb (Rochester, NY), Krolman (Boston, MA), Numedis Inc. (Isanti, MN), or Stephens Instruments (Lexington, KY). In some embodiments, the viewing chamber may include a viewing chamber as described in U.S. Patent Publication No. 2018/0106704 A1.

In some embodiments, the viewing chamber may be composed of a body with a lid that couples to the body.

In some embodiments, when the incised DMEK graft in the viewing chamber is disposed in an injector, the injector can be removably inserted into the viewing chamber. The injector may be coupled to the inner body of the viewing chamber or may lay adjacent to the inner body of the viewing chamber.

In some embodiments, the viewing chamber may include or be formed from a polymer, a glass, or another suitable material.

In some embodiments, the viewing chamber may include a pharmaceutically acceptable carrier. Any suitable pharmaceutically acceptable carrier may be used including, for example, a buffer, a cell culture media, a cell storage media, an excipient, a diluent, a solvent, an accessory ingredient, and/or a stabilizer. In some embodiments, a media may include a corneal storage media. Exemplary corneal storage medias include, for example, OPTISOL-GS (Bausch & Lomb, Rochester, NY), LIFE4° C. (Numedis, Isanti, MN).

Methods of Making

In a further aspect, this disclosure describes a method including making at least two incisions and no more than three incisions to a DMEK graft. In some embodiments, the incisions preferably facilitate formation of a triple scroll conformation by the DMEK graft. As further described in Example 1, the use of these incisions results in a graft that is wider and easier to unscroll than a non-incised graft which forms a single or double scroll.

In some embodiments, the DMEK graft may include three incisions. However, in some embodiments, the DMEK graft preferably has only two incisions.

In some embodiments, the method includes making the incisions before the Descemet's membrane with endothelial cells (that is, the DMEK graft) is harvested from a donor cornea. In some embodiments, the method includes making the incisions after the Descemet's membrane with endothelial cells (that is, the DMEK graft) is harvested from a donor cornea. The method preferably includes making the incisions before the DMEK graft is inserted to the recipient eye.

In some embodiments, the method includes harvesting the DMEK graft from the donor cornea. In some embodiments, the method includes excising the DMEK graft from the rest of the cornea (including the corneolimbal ring) including, for example, by trephining the DMEK graft.

In some embodiments, the method includes making the incisions after the DMEK graft has been excised completely from the rest of the cornea (including the corneolimbal ring) including, for example, by trephination. In some embodiments, the method includes making incisions in the DMEK graft after trephination but before the separation from the rest of the cornea is complete. In some embodiments, the method includes making incisions in the DMEK graft before trephination and before the separation from the rest of the cornea is complete. In some embodiments, the method includes making incisions in the DMEK graft while trephining.

In some embodiments, including when the DMEK graft is prepared by manual peeling of the graft from a donor corneoscleral rim, the incisions may be made at the end of the manual peeling, with the incisions being made opposite the direction of the peel step. In some embodiments, including when the DMEK graft is prepared by manual peeling of the graft from a donor corneoscleral rim, the incisions may be made along the edge opposite the separated portion of the DMEK graft. In some embodiments, the incisions may be made radially, that is, the incisions follow lines that point to a common center. In some embodiments, the incisions may be made along vectors formed by two sides of an isosceles triangle. (See, e.g. FIG. 4E.) In some embodiments, when the incisions are made along vectors formed by two sides of the isosceles triangle, the incisions are made along the two equal length sides of the isosceles triangle. In some embodiments, the incisions may be made along vectors formed by two sides of an equilateral triangle. (See, e.g., FIG. 4C-FIG. 4D.)

In some embodiments, including when the DMEK graft is prepared by fluid or air dissection, the incisions may be made during or after trephination.

In some embodiments, the method includes staining the DMEK graft with a dye including, for example, trypan blue. In some embodiments, the DMEK graft may be stained with a dye before the incisions are made. In some embodiments, a portion of the DMEK graft may be stained with a dye before the incisions are made. In some embodiments, the DMEK graft may be stained with a dye after the incisions are made. In some embodiments, excess dye may be removed from the DMEK graft including, for example, with a sponge.

The incisions may be made with any suitable instrument. In exemplary embodiments, the incisions may be made with a needle, a stab knife, a slit knife, scissors, a punch, or a trephine. In some embodiments, a needle may include a 23-gauge needle, a 25-gauge needle, or a 27-gauge needle. In some embodiments, a stab knife may include a 0.5 mm stab knife, a 1 mm stab knife, or a 1.5 mm stab knife. In some embodiments, a slit knife may include a 0.5 mm slit knife, a 1 mm slit knife, or a 1.5 mm slit knife. In an exemplary embodiment, the incisions may be made with a bevel edge of a 27-gauge needle.

In some embodiments, the incisions are radial incisions, that is, the incisions follow lines that point to a common center. The radial incisions may extend at least 0.3 mm, at least 0.4 mm, at least 0.5 mm, at least 0.6 mm, at least 0.7 mm, at least 0.8 mm, at least 0.9 mm, at least 1 mm towards the center of the graft from the graft edge. In some embodiments, the radial incisions extend up to 0.4 mm, up to 0.5 mm, up to 0.6 mm, up to 0.7 mm, up to 0.8 mm, up to 0.9 mm, up to 1 mm, up to 1.1 mm, up to 1.2 mm, up to 1.3 mm, up to 1.4 mm, up to 1.5 mm, up to 1.6 mm, up to 1.7 mm, up to 1.8 mm, up to 1.9 mm, or up to 2 mm towards the center of the graft from the graft edge. For example, in some embodiments, the incision may extend at least 0.3 mm and up to 2 mm towards the center of the graft from the graft edge. In another exemplary embodiment, the incision may extend at least 0.5 mm and up to 1.6 mm towards the center of the graft from the graft edge.

In some embodiments, the incisions may extend along vectors formed by two sides of an isosceles triangle. (See, e.g. FIG. 4E.) In some embodiments, when the incisions extend along vectors formed by two sides of an isosceles triangle, the incisions extend along the vectors formed of the two equal length sides of the isosceles triangle. In some embodiments, the incisions may extend along vectors formed by two sides of an equilateral triangle. (See, e.g., FIG. 4C-FIG. 4D.) The incisions may extend at least 0.3 mm, at least 0.4 mm, at least 0.5 mm, at least 0.6 mm, at least 0.7 mm, at least 0.8 mm, at least 0.9 mm, at least 1 mm, at least 1.1 mm, at least 1.2 mm, at least 1.3 mm, at least 1.4 mm, at least 1.5 mm from the edge of the graft. In some embodiments, the incisions extend up to 0.4 mm, up to 0.5 mm, up to 0.6 mm, up to 0.7 mm, up to 0.8 mm, up to 0.9 mm, up to 1 mm, up to 1.1 mm, up to 1.2 mm, up to 1.3 mm, up to 1.4 mm, up to 1.5 mm, up to 1.6 mm, up 1.7 mm, up to 1.8 mm, up to 1.9 mm, or up to 2 mm from the edge of the graft. For example, in some embodiments, each incision may extend at least 0.3 mm and up to 2 mm from the edge of the graft along a vector formed one of the two equal length sides of an isosceles triangle or one of the sides of an equilateral triangle. In another exemplary embodiment, each incision may extend at least 0.5 mm and up to 1.6 mm from the edge of the graft along a vector formed one of the two equal length sides of an isosceles triangle or one of the sides of an equilateral triangle.

The distance between the incisions (in degrees) is measured relative to the geometric center of a DMEK graft. Although most DMEK grafts are circular—and the geometric center of the graft would be the center of the circle—some DMEK grafts have an elliptical or ovular shape.

In some embodiments, the incisions are placed at least 45 degrees, at least 50 degrees, at least 55 degrees, at least 60 degrees, at least 65 degrees, at least 70 degrees, at least 75 degrees, at least 80 degrees, at least 85 degrees, at least 90 degrees, at least 95 degrees, at least 100 degrees, at least 105 degrees, at least 110 degrees, at least 115 degrees, or at least 120 degrees apart from each other. In some embodiments, the incisions are placed up to 110 degrees, up to 115 degrees, up to 120 degrees, up to 125 degrees, up to 130 degrees, up to 135 degrees, up to 140 degrees, up to 145 degrees, up to 150 degrees, up to 155 degrees, up to 160 degrees, up to 165 degrees, up to 170 degrees, up to 175 degrees, or up to 180 degrees apart from each other. For example, in some embodiments, the incisions are placed at a distance apart from each other in a range of 80 degrees to 160 degrees. In some embodiments, the incisions are placed at a distance apart from each other in a range of 100 degrees to 140 degrees. In some embodiments, the incisions are placed at a distance apart from each other in a range of 105 degrees to 135 degrees. In some embodiments, the incisions are placed at a distance apart from each other in a range of 110 degrees to 130 degrees. In an exemplary embodiment, the incisions are placed at a distance apart from each other of 120 degrees, as shown in FIG. 4A. In another exemplary embodiment, the incisions are placed at a distance apart from each other of less than 120 degrees, as shown in FIG. 4E.

In some embodiments, the method may include grasping the DMEK graft with forceps. In some embodiments, the forceps may contact the graft at a point between 110 degree and 130 degrees from either incision point. The distance of the incision points from the forceps contact point may help prevent tearing at that incision site when the graft is lifted with forceps.

In some embodiments, the method may include loading the incised DMEK graft into an injector. In some embodiments, the injector includes a glass surface including, for example, a Straiko modified Jones tube (available from Gunther Weiss Scientific Glassblowing Co., Inc., Portland, OR), a pipette as included in a DMEK Disposable Surgical Set (available from DORC, the Netherlands), or a DMEK Cartridge (available from Geuder, Heidelberg, Germany). In some embodiments, the injector includes a plastic surface. In some embodiments, the injector includes a commercially available injector including, for example, an Endoject injector (available from Medicel, Altenrhein, Switzerland) or a DMEK EndoGlide (available from Network Medical, North Yorkshire, UK). In some embodiments, the glass surface or the plastic surface may be in contact with the corneal endothelial cells of the DMEK graft.

In an exemplary embodiment, the DMEK graft is prepared by manual peeling. When the graft is prepared by manual peeling, part of the graft (for example, a quarter of the graft) may remain attached on one side. Preparing may include, for example, scoring (for example, using a reverse Sinskey hook) and/or stripping (for example, with a 90° scraper). Trypan blue may be used to stain the edge of Descemet's membrane. Excess trypan may be removed (for example, with a sponge). The graft is then punched with a trephine of the desired size. The rim of cut Descemet's membrane may then be removed. The incisions are then made. If the graft remains attached, the incisions are made along the side where the graft remains attached. The incised graft is then grasped (for example, with forceps) and removed from the corneal stroma before being stained in trypan and loaded into an injector. The injector may then be placed into a viewing chamber for storing and/or evaluating the tissue.

In another exemplary embodiment, the DMEK graft may be prepared by air or fluid dissection. Preparing may include, for example, injection of air, balanced salt solution, trypan blue, corneal storage media or other suitable fluid into the interstitial space in posterior stroma to exert a pressure which initiates the separation of Descemet's membrane from posterior stroma. This separation can be expanded for example with air, balanced salt solution, trypan blue, corneal storage media or other suitable fluid to the full size of the Descemet's membrane. Air or fluid is drained through an opening in the dissected Descemet membrane. The graft is then punched with a trephine of the desired size. The rim of cut Descemet's membrane may then be removed. The incisions may then be made. The incised graft is then grasped (for example, with forceps) and removed from the corneal stroma before being stained in trypan and loaded into an injector. The injector may then be placed into a viewing chamber for storing, evaluating, and/or distributing the tissue.

Methods of Using

In another aspect, this disclosure describes a method including using a DMEK graft as described herein in an Endothelial Keratoplasty (EK) procedure. In a further aspect, this disclosure describes a method including using an injector including a DMEK graft, as described herein.

In some embodiments, the incised DMEK graft may be injected into the anterior chamber of the eye through a surgical incision. The incised DMEK graft may be injected in a single, double, or triple scroll conformation with endothelial cells on the outer surface of the scroll. Once injected, the incised DMEK graft favors a triple scroll conformation, with the graft assuming the triple scroll conformation resulting in a widening of the graft. Tapping the top of the cornea and providing bursts of balanced salt solution may be used to help the graft achieve the desired triple scroll conformation. Because the central planar region of the triple scroll conformation is larger than a single scroll or double scroll conformation, less manipulation by a surgeon is required to finish unscrolling the graft, allowing the EK procedure to be completed more quickly. Once the graft assumes a triple scroll conformation, an air bubble may be placed under the graft to bring it into contact with the posterior stroma.

In an exemplary embodiment, a full thickness incision is made in the cornea and the incised DMEK graft is injected into the anterior chamber of the eye through the incision in the cornea. In some embodiments, the incised DMEK graft may be placed by the surgeon in an injection cartridge. Additionally or alternatively, the incised DMEK graft may be provided to the surgeon in an injection cartridge encased in a viewing chamber. In other embodiments, the incised DMEK graft may be provided to the surgeon in an injection cartridge. Additionally or alternatively, the incised DMEK graft may be provided to the surgeon in an injection cartridge encased in a viewing chamber. After injection, the main incision may be sutured. The incised DMEK graft is manipulated until a trifold configuration is achieved, including, for example, by using gentle strokes on the cornea with a cannula. Once the graft assumes the trifold configuration, air is placed posterior to the graft. Portions of the graft edge may be unfolded by the posterior support of the air bubble. The anterior chamber may then be filled with gas or air.

In a case series transplanting ten DMEK grafts into a cadaver eye, it was shown that operative times significantly decreased with the addition of paired radial incisions. Grafts were initially transplanted without the presence of incision. These grafts were then removed and re-prepped with the addition of paired radial incisions. The average surgical time to center and unscroll a DMEK graft without the addition of radial incisions was 5 minutes and 26 seconds. This time was reduced to 2 minutes and 36 seconds with the addition of paired incisions to the graft ($p<0.05$).

EXEMPLARY EMBODIMENTS

Embodiment 1

A composition for corneal transplantation comprising:
a Descemet's Membrane Endothelial Keratoplasty (DMEK) graft comprising two incisions;
wherein the DMEK graft comprises Descemet's membrane and corneal endothelial cells;
wherein the DMEK graft has a geometric center; and
wherein the two incisions are placed at a distance apart from each other in a range of 105 degrees to 135 degrees, the distance between the incisions being measured relative to the geometric center of the DMEK graft.

Embodiment 2

The composition of Embodiment 1, wherein the two incisions are placed at a distance apart from each other in a range of 115 degrees to 125 degrees.

Embodiment 3

The composition of any one of the preceding Embodiments, wherein the DMEK graft does not comprise more than three incisions.

Embodiment 4

The composition of any one Embodiments 1 to 3, wherein the DMEK graft comprises a graft edge, and wherein each incision extends towards the geometric center of the DMEK graft from the graft edge.

Embodiment 5

The composition of any one of Embodiments 1 to 3, wherein the DMEK graft comprises a graft edge, and wherein each incision extends from the graft edge along a vector formed a side of an isosceles triangle or an equilateral triangle.

Embodiment 6

The composition of Embodiment 4 or Embodiment 5, wherein each incision extends at least 0.3 mm and up to 2 mm from the graft edge.

Embodiment 7

The composition of any one of the preceding Embodiments, wherein the DMEK graft does not comprise a corneolimbal ring.

Embodiment 8

The composition of any one of the preceding Embodiments, wherein the DMEK graft comprises a dye.

Embodiment 9

The composition of any one of the preceding Embodiments, wherein the DMEK graft comprises an orientation mark.

Embodiment 10

The composition of any one of the preceding Embodiments, wherein the DMEK graft in a stable submerged conformation forms a circumcircle of a triangle with the triangle forming a mostly planar region, and wherein the circumcircle comprises segments of the circle outside the triangle, wherein the segments fold towards the center of the circumcircle.

Embodiment 11

The composition of Embodiment 10, wherein the graft width, as measured along the shortest side of the triangle is at least 2000 microns, at least 3000 microns, at least 4000 microns, at least 5000 microns, at least 6000 microns, or at least 7000 microns.

Embodiment 12

The composition of any one of the preceding Embodiments, wherein the DMEK graft comprises tissue from a donor having an age of at least 20 years and up to 90 years.

Embodiment 13

The composition of any one of the preceding Embodiments, the composition further comprising a pharmaceutically acceptable carrier.

Embodiment 14

An injector comprising the composition of any one of the preceding Embodiments.

Embodiment 15

The injector of Embodiment 14, the injector comprising a glass surface or a plastic surface.

Embodiment 16

A viewing chamber comprising the composition of any one of Embodiments 1 to 13.

Embodiment 17

A viewing chamber comprising the injector of Embodiment 14 or 15.

Embodiment 18

A method comprising using the injector of any one of Embodiments 14, 15, or 17.

Embodiment 19

A method of making the composition of any one of Embodiments 1 to 13.

Embodiment 20

A method of using the composition of any one of Embodiments 1 to 13.

Embodiment 21

A method comprising
providing a Descemet's Membrane Endothelial Keratoplasty (DMEK) graft comprising Descemet's membrane and corneal endothelial cells; and
making two incisions to the DMEK graft to form an incised DMEK graft;
wherein the DMEK graft has a geometric center, and wherein the two incisions are placed at a distance apart from each other in a range of 105 degrees to 135 degrees, the distance between the incisions being measured relative to the geometric center of the DMEK graft.

Embodiment 22

The method of Embodiment 21, wherein when the DMEK graft is in a stable submerged conformation, the incised DMEK graft forms a circumcircle of a triangle with the triangle forming a mostly planar region, and wherein the circumcircle comprises segments of the circle outside the triangle, wherein the segments fold towards the center of the circumcircle.

Embodiment 23

The method of Embodiment 21, wherein the graft width, as measured along the shortest side of the triangle is at least 2000 microns, at least 3000 microns, at least 4000 microns, at least 5000 microns, at least 6000 microns, or at least 7000 microns.

Embodiment 24

The method any one of Embodiments 21 to 23, wherein the method comprises making no more than three incisions.

Embodiment 25

The method of any one of Embodiments 21 to 24, wherein the method further comprising harvesting the DMEK graft from a donor cornea.

Embodiment 26

The method of Embodiment 25, wherein the method further comprises trephining the DMEK graft.

Embodiment 27

The method of any one of Embodiments 21 to 26, wherein the method comprises staining the DMEK graft with a dye.

Embodiment 28

The method of any one of Embodiments 21 to 27, wherein the DMEK graft comprises a graft edge, and wherein each incision extends towards the geometric center of the DMEK graft from the graft edge.

Embodiment 29

The method of any one of Embodiments 21 to 27, wherein the DMEK graft comprises a graft edge, and wherein each incision extends from the graft edge along a vector formed by a side of an isosceles triangle or an equilateral triangle.

Embodiment 30

The method of Embodiment 28 or 29, wherein each incision extends at least 0.3 mm and up to 2 mm from the graft edge.

Embodiment 31

The method of any one of Embodiments 21 to 30, the method comprising grasping the DMEK graft with forceps at a point between 105 degrees and 135 degrees from either incision point.

Embodiment 32

The method of any one of Embodiments 21 to 31, the method comprising loading the DMEK graft into an injector.

Embodiment 33

The method of any one of Embodiments 21 to 31, the method comprising loading the DMEK graft into a viewing chamber.

Embodiment 34

The method of Embodiment 32, the method comprising loading the injector into a viewing chamber.

Embodiment 35

A method comprising injecting an incised Descemet's Membrane Endothelial Keratoplasty (DMEK) graft into the anterior chamber of an eye,
wherein the incised DMEK graft comprises Descemet's membrane and corneal endothelial cells;
wherein the incised DMEK graft comprises two incisions;
wherein the DMEK graft has a geometric center; and
wherein the two incisions are placed at a distance apart from each other in a range of 105 degrees to 135 degrees, the distance between the incisions being measured relative to the geometric center of the DMEK graft.

Embodiment 36

The method of Embodiment 35, wherein the method comprises injecting an incised DMEK graft from an injector comprising the incised DMEK graft.

Embodiment 37

The method of Embodiment 35 or 36, wherein the incised DMEK graft comprises no more than three incisions.

Embodiment 38

An injector comprising an incised Descemet's Membrane Endothelial Keratoplasty (DMEK) graft,
  wherein the incised DMEK graft comprises Descemet's membrane and corneal endothelial cells;
  wherein the incised DMEK graft comprises two incisions;
  wherein the DMEK graft has a geometric center; and
  wherein the two incisions are placed at a distance apart from each other in a range of 105 degrees to 135 degrees, the distance between the incisions being measured relative to the geometric center of the DMEK graft.

Embodiment 39

The injector of Embodiment 38, wherein the incised DMEK graft comprises no more than three incisions.

Embodiment 40

The injector of Embodiment 38 or 39, wherein the injector comprises a surface, the surface comprising glass or plastic, and the surface being in contact with the corneal endothelial cells of the DMEK graft.

Embodiment 41

The injector of any one of Embodiment 38 to 40, wherein the injector further comprises a pharmaceutically acceptable carrier.

Embodiment 42

The injector of any one of Embodiments 38 to 41, wherein the incised DMEK graft does not comprise corneolimbal ring tissue.

Embodiment 43

The injector of any one of Embodiments 38 to 42, wherein the incised DMEK graft is stained with a dye.

Embodiment 44

The injector of any one of Embodiments 38 to 43, wherein the incised DMEK graft comprises an orientation mark.

Embodiment 45

A viewing chamber comprising the injector of any one of Embodiments 38 to 44.

Embodiment 46

A viewing chamber comprising
  an injector comprising an incised Descemet's Membrane Endothelial Keratoplasty (DMEK) graft;
  wherein the incised DMEK graft comprises Descemet's membrane and corneal endothelial cells;
  wherein the incised DMEK graft comprises two incisions;
  wherein the DMEK graft has a geometric center; and
  wherein the two incisions are placed at a distance apart from each other in a range of 105 degrees to 135 degrees, the distance between the incisions being measured relative to the geometric center of the DMEK graft.

The present invention is illustrated by the following examples. It is to be understood that the particular examples, materials, amounts, and procedures are to be interpreted broadly in accordance with the scope and spirit of the invention as set forth herein.

EXAMPLES

Example 1

This Example describes the effect of paired radial incisions on unscrolling of DMEK grafts. Use of these incisions results in a graft that is wider and easier to unscroll than a typical single or double scrolled graft. This Example further describes the efficacy of using paired incisions to achieve a triple scroll conformation in DMEK grafts and the impact of incision length and donor age on folding patterns.

Methods

Corneas from donors aged ≥18 years of age without endothelial scars were obtained from Lions Gift of Sight (St. Paul, MN). For corneas from donors aged ≥50 years of age, Descemet's membrane (DM) was peeled from cornea using a standard SCUBA (submerged cornea using backgrounds away) technique (Parekh et al. *Cornea.* 2017; 36:1458-1466). For corneas from donors aged <50 years, Descemet's membrane was fluid dissected from the cornea using a bubble technique (Feizi S, Javadi M A. *Eur J Ophthalmology* 2016; 26:6-11).

After separation from the cornea, the DMEK grafts were trephined using a 7.75 mm suction-trephine block. All grafts were stained with trypan blue 0.06% for 3 minutes. Grafts were then submerged in a balanced salt solution (BSS), allowed to scroll, and imaged.

Figure 6A:
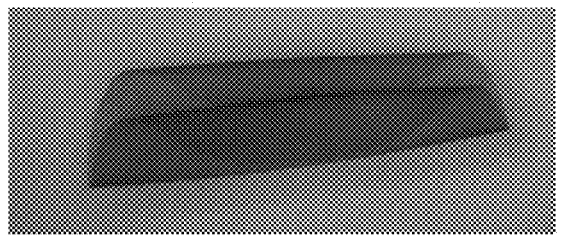
FIG. 6A shows a DMEK graft in a native double scroll conformation.
Figure 6B:
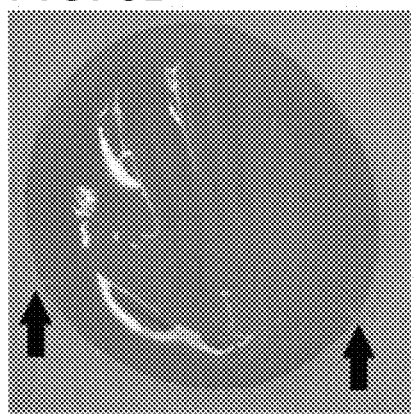
FIG. 6B shows the graft after a pair of radial incisions (arrows) with incision length 0.5 mm are added. The incisions are indicated by the black arrows. After the incisions are made, the graft adopts a triple scroll conformation where the edge of the graft hinges (asterisk) on the two incisions, as shown in FIG. 6C. After extension of the radial incisions to 1.0 mm or 1.5 mm, indicated by black arrows in FIG. 6D and FIG. 6F, respectively, the graft maintains its triple scroll conformation, as shown in FIG. 6E and FIG. 6G, respectively.

Each graft was then flattened on a petri dish, and a pair of radial incisions were cut into the edge of the graft with the bevel edge of a 27-gauge needle. Incisions were placed 120° apart with an incision length of 0.5 mm (FIG. 4, FIG. 6B).

Figure 6C:
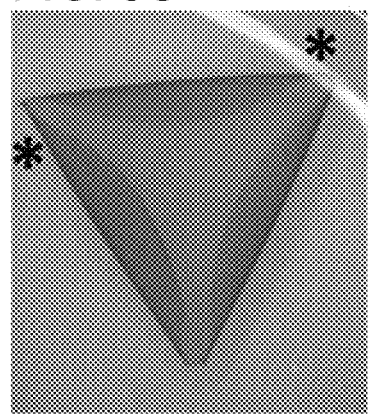

The graft was then lifted from the edge of the graft away from the incisions and placed back into BSS. The graft was encouraged to triple scroll by holding onto the opposite side of the graft until the graft was completely submerged, then releasing. The graft was then given 60 seconds to reach a stable conformation and re-imaged (FIG. 6C).

Figure 6D:
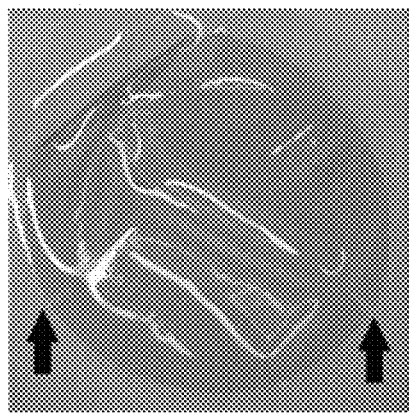
Figure 6E:
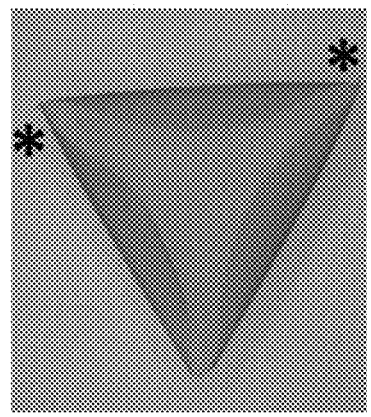

Each DMEK graft was then flattened a second time. The initial radial incisions were extended to 1.0 mm in length FIG. 6D). The graft was then re-submerged, allowed to scroll again, and re-imaged (FIG. 6E).

Figure 6F:
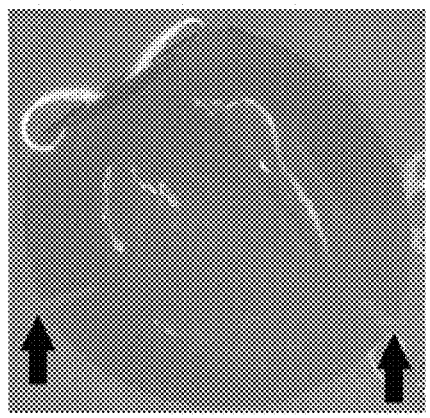
Figure 6G:
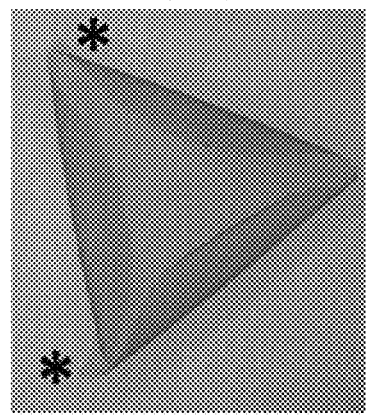

Each DMEK graft was then flattened a third time, and the radial incision length was extended to 1.5 mm (FIG. 6F). The graft was then re-submerged, allowed to scroll again, and re-imaged (FIG. 6G).

Images were then reviewed for scrolling patterns (single scroll, double scroll, or triple scroll). Graft width was measured for each image using tracing tools in ImageJ software (National Institutes of Health, Rockville, MD). Images were calibrated against a standardized image of a stage micrometer. For single and double scrolls, graft width was measured at the widest point of the scroll. For triple scrolls, graft width was measured along the shortest side of the triangle as viewed en face. The impact of donor age and incision length on scrolling patterns and graft width was evaluated to determine optimal parameters for achieving a DMEK graft triple scroll.

Results

As shown in Table 1, a stable triple scroll was achieved under at least one incision condition in 100% (10/10) of donor grafts age ≤65 years, compared to 0% (0/4) of donor grafts age >65 years. For donor grafts age ≤65 years, 60% (6/10) achieved a stable triple scroll with an incision length of 0.5 mm; and 80% (8/10) achieved a stable triple scroll with incision length of 1.0 mm, and 60% (6/10) achieved at stable triple scroll with an incision length of 1.5 mm.

As shown in Table 2, a post-hoc Tukey test revealed a significant difference between the graft widths between the natural scroll and each of the incision lengths (0.5 mm, 1.0 mm, and 1.5 mm) (p<0.002). This remained significant with further sub-analysis of grafts age <65 years (p<0.002).

As shown in FIG. 7, pre-incision graft width increased with increasing donor age. Post-incision, only grafts that remained single or double scrolls (failed to form triple scrolls) showed a similar statistically significant increase in graft width with increasing donor age.

TABLE 1

DMEK Folding Patterns

| Donor Age | No Incisions (Scroll) | Incision (mm) | | |
|---|---|---|---|---|
| | | 0.5 | 1.0 | 1.5 |
| 39 | Double | O | T | T |
| 43 | Double | O | T | T |
| 51 | Double | O | O | T |
| 55 | Single | T | T | O |
| 55 | Single | T | T | T |
| 57 | Single | T | T | T |
| 58 | Double | T | T | O |
| 58 | Single | O | O | T |
| 59 | Double | T | T | T |
| 61 | Double | T | T | T |
| 68 | Single | O | O | O |
| 70 | Single | O | O | O |
| 71 | Single | O | O | O |
| 77 | Single | O | O | O |

T = Triple Scroll
O = No Triple Scroll

TABLE 2

Graft Width vs. Incision Length

| Incision (mm) | Mean Graft Width (μm) | p value |
|---|---|---|
| All Grafts | | |
| Natural Scroll | 1563 ± 428 | |
| 0.5 mm Incision | 3924 ± 2369 | <0.002 |
| 1.0 mm Incision | 3961 ± 2229 | <0.001 |
| 1.5 mm Incision | 3687 ± 1912 | <0.002 |
| Grafts ≤65 Years | | |
| Natural Scroll | 1456 ± 503 | |
| 0.5 mm Incision | 4390 ± 2506 | <0.002 |
| 1.0 mm Incision | 4814 ± 2188 | <0.001 |
| 1.5 mm Incision | 4367 ± 1933 | <0.001 |

DISCUSSION

This Example describes testing of a new approach of using small paired radial incisions to widen a DMEK scroll and facilitate unscrolling. This technique shows significant promise in surgical use including reducing the learning curve and surgical time for DMEK surgeons-in-training.

The results of this study demonstrate that the use of paired incisions, with 120° of separation, encourages a wide, triple scroll conformation in a DMEK graft that is favorable for unfolding or unscrolling during surgery to introduce the graft. This conformation occurs because the DMEK graft tends to hinge at the paired incision sites, which locks in two vertices of an equilateral triangle (FIG. 4). The hinging prevents the graft from going into a typical scroll and allows the graft to form a triple scroll. A third incision at the final vertex of the triangle is avoided because of the risk of tearing at that incision site when the graft is lifted with forceps from that location.

Paired incisions may be more effective in younger tissue (age ≤65) due to older tissues not scrolling tightly enough to catch and hinge on the incisions.

Moreover, extending the incision length was not shown to increase the likelihood of achieving a triple scroll. However, in the tissue from younger donor (age ≤50 years), the 1.0 mm and 1.5 mm incisions were more effective at inducing a triple scroll than the 0.5 mm incisions (see Table 1).

This study demonstrated a significant, 2.6-fold increase in graft width among grafts that adopted a triple scroll conformation compared to baseline scrolls. In contrast, for grafts that did not achieve a triple scroll conformation, there was no statistical difference in graft width compared to baseline scrolls. These results suggest that for the incisions to have a significant impact on graft width, a triple scroll conformation must be achieved.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A composition for corneal transplantation comprising:
   a Descemet's Membrane Endothelial Keratoplasty (DMEK) graft comprising two incisions, three scrolling axes, and a triple scroll conformation;
   wherein the DMEK graft comprises Descemet's membrane and corneal endothelial cells;
   wherein the DMEK graft has a geometric center; and wherein the two incisions are placed at a distance apart from each other in a range of 105 degrees to 135 degrees, the distance between the incisions being measured relative to the geometric center of the DMEK graft.

2. The composition of claim 1, wherein the two incisions are placed at a distance apart from each other in a range of 115 degrees to 125 degrees.

3. The composition of claim 1, wherein the DMEK graft does not comprise more than three incisions.

4. The composition of claim 1, wherein the DMEK graft comprises a graft edge; and wherein each incision extends at least 0.3 mm and up to 2 mm towards the geometric center of the DMEK graft from the graft edge.

5. The composition of claim 1, wherein the DMEK graft comprises a graft edge; and wherein each incision extends at least 0.3 mm and up to 2 mm from the graft edge along a vector formed by a side of an isosceles triangle or an equilateral triangle.

6. The composition of claim 1, wherein the DMEK graft does not comprise a corneolimbal ring.

7. The composition of claim 1, wherein the DMEK graft comprises a dye.

8. The composition of claim 1, wherein the DMEK graft comprises an orientation mark.

9. The composition of claim 1, wherein the DMEK graft comprises tissue from a donor having an age of at least 20 years and up to 90 years.

10. An injector comprising the composition of claim 1.

11. A viewing chamber comprising the composition of claim 1.

12. A method comprising
providing a Descemet's Membrane Endothelial Keratoplasty (DMEK) graft comprising Descemet's membrane and corneal endothelial cells; and
making two incisions to the DMEK graft to form an incised DMEK graft comprising three scrolling axes and a triple scroll conformation;
wherein the DMEK graft has a geometric center, and wherein the two incisions are placed at a distance apart from each other in a range of 105 degrees to 135 degrees, the distance between the incisions being measured relative to the geometric center of the DMEK graft.

13. The method of claim 12, wherein the method comprises making no more than three incisions.

14. The method of claim 12, wherein the method comprises harvesting the DMEK graft from a donor cornea.

15. The method of claim 12, wherein the method comprises trephining the DMEK graft.

16. The method of claim 12, wherein the method comprises staining the DMEK graft with a dye.

17. The method of claim 12, wherein the DMEK graft comprises a graft edge, and wherein each incision extends at least 0.3 mm and up to 2 mm towards the geometric center of the DMEK graft from the graft edge.

18. The method of claim 12, wherein the DMEK graft comprises a graft edge, and wherein each incision extends at least 0.3 mm and up to 2 mm from the graft edge along a vector formed by a side of an isosceles triangle or an equilateral triangle.

19. The method of claim 12, the method further comprising loading the DMEK graft into an injector or a viewing chamber or both.

20. A composition for corneal transplantation comprising:
a Descemet's Membrane Endothelial Keratoplasty (DMEK) graft comprising two incisions and three scrolling axes
wherein the DMEK graft comprises Descemet's membrane and corneal endothelial cells;
wherein the DMEK graft has a geometric center and a graft edge, and wherein each incision extends at least 0.3 mm and up to 2 mm towards the geometric center of the DMEK graft from the graft edge; and
wherein the two incisions are placed at a distance apart from each other in a range of 105 degrees to 135 degrees, the distance between the incisions being measured relative to the geometric center of the DMEK graft.

21. The composition of claim 20, wherein the two incisions are placed at a distance apart from each other in a range of 115 degrees to 125 degrees.

22. The composition of claim 20, wherein the DMEK graft does not comprise more than three incisions.

23. The composition of claim 20, wherein the DMEK graft does not comprise a corneolimbal ring.

24. The composition of claim 20, wherein the DMEK graft comprises a dye.

25. The composition of claim 20, wherein the DMEK graft comprises an orientation mark.

26. The composition of claim 20, wherein the DMEK graft comprises tissue from a donor having an age of at least 20 years and up to 90 years.

27. An injector comprising the composition of claim 20.

28. A viewing chamber comprising the composition of claim 20.

29. A composition for corneal transplantation comprising:
a Descemet's Membrane Endothelial Keratoplasty (DMEK) graft comprising two incisions and three scrolling axes;
wherein the DMEK graft comprises Descemet's membrane and corneal endothelial cells;
wherein the DMEK graft has a geometric center and a graft edge, and wherein each incision extends at least 0.3 mm and up to 2 mm from the graft edge along a vector formed by a side of an isosceles triangle or an equilateral triangle; and
wherein the two incisions are placed at a distance apart from each other in a range of 105 degrees to 135 degrees, the distance between the incisions being measured relative to the geometric center of the DMEK graft.

30. The composition of claim 29, wherein the two incisions are placed at a distance apart from each other in a range of 115 degrees to 125 degrees.

31. The composition of claim 29, wherein the DMEK graft does not comprise more than three incisions.

32. The composition of claim 29, wherein the DMEK graft does not comprise a corneolimbal ring.

33. The composition of claim 29, wherein the DMEK graft comprises a dye.

34. The composition of claim 29, wherein the DMEK graft comprises an orientation mark.

35. The composition of claim 29, wherein the DMEK graft comprises tissue from a donor having an age of at least 20 years and up to 90 years.

36. An injector comprising the composition of claim 29.

37. A viewing chamber comprising the composition of claim 29.

* * * * *